United States Patent
Coats et al.

(10) Patent No.: US 6,545,043 B1
(45) Date of Patent: *Apr. 8, 2003

(54) COMPOUNDS RELATED TO NATURAL SOURCES AND THEIR USE AS BIOPESTICIDES

(75) Inventors: Joel R. Coats, Ames, IA (US); Christopher J. Peterson, Ames, IA (US); Rong Tsao, Guelph (CA); Aimee L. Eggler, Madison, WI (US); Gregory L. Tylka, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/583,481

(22) Filed: May 31, 2000

Related U.S. Application Data

(63) Continuation-in-part of application No. 08/828,190, filed on Mar. 22, 1997, now Pat. No. 6,207,705.

(51) Int. Cl.$^7$ .......................... A01N 47/40; A01N 37/34

(52) U.S. Cl. ...................... 514/514; 514/519; 514/526; 514/527

(58) Field of Search ................................ 514/514, 519, 514/526, 527

(56) References Cited

U.S. PATENT DOCUMENTS

| 4,173,567 A | 11/1979 | Findeisen et al. ............ 548/216 |
| 5,885,809 A | 3/1999 | Effenberger et al. ......... 435/128 |

OTHER PUBLICATIONS

Brown et al, Gas Chromatography of Allelochemicals Produced During Glucosinolate Degradation in Soil, J. Agric. Food Chem., 42, pp. 2029–2034, 1994.*

Tsao et al, Insecticidal Toxicities of Glucosinolate–Containing Extracts from Crambe Seeds, J. Agric. Entomol., 13(2), pp. 109–120, 1996.*

Catalog Handbook of Fine Chemicals ALDRICH, "CHP–acetate" (carboxyester of CHP) 27,962–5, 14, (1998–1999).

Goodman And Gilman's The Pharmacological Basis of Therapeutics, Seventh Edition, A.G. Gilman, et al., editors, MacMillan Publishing Company, New York, NY, pp. 149, 159–162, (1985).

"Products & Services—Review of Plant Pathology", CABI—Publications Catalogue, http://www.cabi.org/catalog/journals/absjour/Om.htm, 2 p., (May 31, 2000).

Alef, K., et al., "Rapid and Sensitive Determination of Microbial Activity in Soils and in Soil Aggregates by Dimethylsulfoxide Reduction", Biology and Fertility of Soils, vol. 8, pp. 349–355, (1989).

Anderson, T.A., et al., "Fate of Methyl Bromide in Fumigated Soils", Fumigants—Environmental Fate, Exposure, and Analysis, Chapter 5, ACS Symposium Series: 652, pp. 42–52, (1997).

Andrews, L.S., et al., "Toxic Effects of Solvents and Vapors", Casarett and Doull's Toxicology, Third Edition, MacMillan Publishing Company, New York, NY, pp. 640–642, 648–649, & 658, (1986).

Bell, J.M., et al., "Histopathology of Thyroids and Livers of Rats and Mice Fed Diets Containing Brassica Glucosinolates", Can. J. Anim. Sci., 52, pp. 395–406, (Jun. 1972).

Bjerg, B., et al., "New Principles of Ion–Exchange Techniques Suitable to Sample Preparation and Group Separation of Natural Products Prior to Liquid Chromatography", Journal of Liquid Chromatography, 7, pp. 691–707, (1984).

Blau, P.A., et al., "Allylglucosinolate and Herbivorous Catapillars: A Contrast in Toxicity and Tolerance", Science, 200, pp. 1296–1298, (1978).

Bodnaryk, R.P., "Developmental Profile of Sinalbin (p–Hydroxybenzyl Glucosinolate) in Mustard Seedlings, Sinapsis alba L., and its Relationship to Insect Resistance", Journal of Chemical Ecology, 17, pp. 1543–1556, (1991).

Borek, V., et al., "Allelochemicals Produced During Sinigrin Decomposition in Soil", J. Agric. Food Chem., 42, pp. 1030–1034, (1994).

Brown, P.D., et al., "Gas Chromatography of Allelochemicals Produced During Glucosinolate Degradation in Soil", J. Agric. Food Chem., 42, pp. 2029–2034, (1994).

Brown, P.D., et al., "Glucosinolate–Containing Plant Tissues as Bioherbicides", J. Agric. Food Chem., 43, pp. 3070–3074 (1995).

Coats, J.R., "Pesticide Degradation Mechanisms and Environmental Activation", Pesticide Transformation Products—Fate and Significance in the Environment, Chapter 2, American Chemical Society, Washington D.C., pp. 10–30, (1991).

Coats, J.R., "Risks From Natural Versus Synthetic Insecticides", Annu. Rev. Entomol., 39, pp. 489–515, (1994).

(List continued on next page.)

Primary Examiner—Alton N. Pryor
(74) Attorney, Agent, or Firm—Schwegman, Lundberg, Woessner & Kluth, P.A.

(57) ABSTRACT

A method for suppressing target pests, comprising exposing the pests to an effective biopesticidal amount of a composition, the composition comprising a carrier and a purified glucosinolate breakdown product having a hydroxyl group attached, wherein a starting material for the purified glucosinolate breakdown product is isolated from a crambe plant or mustard plant, further wherein the target pests are plants, fungi, bacteria or root knot nematodes is disclosed. Methods for suppressing target pests without limitation as to the starting materials are also disclosed wherein the pests are exposed to an effective biopesticidal amount of a composition comprising a carrier and either an analog or a derivative of a purified glucosinolate breakdown product having a hydroxyl group attached.

24 Claims, 2 Drawing Sheets

OTHER PUBLICATIONS

Coats, J.R., et al., "Toxicity and Neurotoxic Effects of Monoterpenoids in Insects and Earthworms", *Naturally Occurring Pest Bioregulators*, Chapter 20, ACS Symposium Series: 449, pp. 306–316, (1991).

Cooper, J., "Rapid Method for Counting Antibiotic–Resistant Rhizobia in Soils", *Soil Biol. Biochem*, 11, pp. 433–435, (1979).

David, W.A., et al., "Mustard Oil Glucosides as Feeding Stimulants for Pieris Brassicae Larvae in a Semi–Synthetic Diet", *Ent. Exp. & Appl.*, 9, pp. 247–255, (1966).

Dawson, G.W., et al., "Chemical Precursors for Studying the Effects of Glucosinolate Catabolites on Diseases and Pests of Oilseed Rape (*Brassica napus*) or Related Plants", *Pestic. Sci.*, 39, pp. 271–278, (1993).

Duncan, A.J., "Glucosinolates", *In: Toxic Substances in Crop Plants*, Chapter 6, J.P. Felix D'Mello, et al., eds., Royal Society of Chemistry, Cambridge, England, pp. 126–147, (1991).

Fenwick, G.R., et al., "Glucosinolates and Their Breakdown Products in Food and Food Plants", *CRC Critical Reviews in Food Science and Nutrition*, 18, pp. 123–201, (1983).

Fenwick, G.R., et al., "Rapeseed Meal and Its Use in Poultry Diets, A Review", *Animal Feed Science and Technology*, 5, pp. 255–298, (1980).

Finch, S., "Volatile Plant Chemicals and Their Effect on Host Plant Findings by the Cabbage Root Fly (*Delia brassicae*)", *Ent. Exp. & Appl.*, 24, pp. 150–159, (1978).

Hedin, P.A., "Developing Research Trends in the Chemistry of Plant Resistance to Pests", *Natural Resistance of Plants to Pests*, ACS Symposium Series, American Chemical Society, Wshington, D.C., pp. 2–14, (1986).

Karr, L.L., et al., "Effects of Four Monoterpenoids on Growth and Reproduction of the German Cockroach (Blattodea: Blattellidae)", *Journal of Economic Entomology*, 85, pp. 424–429, (1992).

Karr, L.L., et al., "Insecticidal Properties of d–Limonene", *J. Pesticide Sci.*, 13, pp. 287–290, (1988).

Karr, L.L., et al., "Toxic Effects of d–Limonene in the Earthworm *Eisenia fetida* (Savigny)", *Pesticide Biochemistry and Physiology*, 36, pp. 175–186, (1990).

Keeton, W.T., et al., "The Origin and Early Evolution of Life", *In: Biological Science*, Fourth Edition, W.T. Keeton, et al., ed., W.W. Norton & Company, pp. 1017–1021, (1986).

Kirk–Othmer, "Insect Control Technology", *Encyclopedia of Chemical Technology*, Fourth Edition,14, pp. 524–579.

Kruger, E.L., et al., "Relative Mobilities of Atrazine, Five Atrazine Degradates, Metolachlor, and Simazine in Soils of Iowa", *Environmental Toxicology and Chemistry*, 15, pp. 691–695, (May 1996).

Lazzeri, L., et al., "In Vitro Activity of Some Glucosinolates and Their Reaction Products Toward a Population of the Nematode *Heterodera schachtii*", *J. Agric. Food Chem.*, 41, pp. 825–829, (1993).

Lee, S., et al., "Insecticidal Properties of Monoterpenoids Against Some Insect Species", *Picogram and Abstracts*, 45, Abstract No. 50 (Agro), 1 p., (1993).

Liener, I.E., "Toxic Constituents of Plant Foodstuffs—2nd Edition", *Toxic Consitutents of Plant Foodstuffs*, 2nd Edition, Academic Press, Harcourt Brace Jovanovich, pp. 102–143, (1980).

Murphy, S.D., "Toxic Effects of Pesticides", *Casarett and Doull's Toxicology*, Third Edition, Chapter 18, MacMillan Publishing Company, New York, NY, pp. 559–560, (1986).

Nair, K.S., et al., "Host Selection by the Adult Cabbage Maggot, *Hylemya brassicae* (Diptera: Anthomyiidae): Effect of Glucosinolates and Common Nutrients on Oviposition", *The Canadian Entomologist*, 108, pp. 1021–1030, (1976).

Nair, K.S., et al., "The Relationship Between Glucosinolate Contest of Cruciferous Plants and Oviposition Preferences of *Hylemya brassicae* (Diptera: Anthomyiidae)", *The Canadian Entomologist*, 108, pp. 1031–1036, (1976).

Nayar, J.K., et al., "Further Investigations into the Chemical Basis of Insect–Host Plant Relationships in an Oligophagous Insect, *Plutella maculipennis* (Curtis) (Lepidoptera: Plutellidae)", *Canadian Journal of Zoology*, 41, pp. 923–929, (1963).

Norton, S., "Toxic Responses of the Central Nervous System", *Casarett and Doull's Toxicology*, Third Edition, Chapter 13, MacMillan Publishing Company, New York, NY, p. 375, (1986).

Oremland, R.S., et al., "Degradation of Methyl Bromide by Methanotrophic Bacteria in Cell Suspensions and Soils", *Applied and Environmental Microbiology*, 60 (10), pp. 3640–3646, (Oct. 1994).

Potts, A.M., "Toxic Responses of the Eye", *Casarett and Doull's Toxicology*, Third Edition, Chapter 17, Macillan Publishing Company, New York, NY, p. 503, (1986).

Raven, P.H., et al., "Bacteria", *In: Biology of Plants*, Fourth Edition, P.H. Raven, et al., Ed., Worth Publishers, Inc., pp. 165, 180–181, (1986).

Rice, P.J., et al., "Insecticidal Properties of Monoterpenoid Derivatives to the House Fly (Diptera: Muscidae) and Red Flour Beetle (Coleoptera: Tenebrionidae)", *Pestic, Sci.*, 41, pp. 195–202, (1994).

Rice, P.J., et al., "Insecticidal Properties of Several Monoterpenoids to the House Fly (Diptera: Muscidae), Red Flour Beetle (Coleoptera: Tenebrionidae), and Southern Corn Rootwork (Coleoptera: Chrysomelidae)", *J. of Economic Entomology*, 87 (5), pp. 1172–1179, (1994).

Rice, P.J., et al., "Structural Requirements for Monoterpenoid Activity Against Insects", *Bioregulators for Crop Protection and Pest Control*, P.A. Hedin, ed., ACS Symposium Series: 557, American Chemical Society, Washington, D.C., pp. 92–108, (1994).

Rice, P.J., et al., "The Influence of Soil Environmental Variables on the Degradation and Volatility of Methyl Bromide in Soil", *Environmental Toxicology and Chemistry*, 15 (10), pp. 1723–1729, (1996).

Somasundaram, L., et al., "Pesticide Transformation Products in the Environment", *Pesticide Transformation Products—Fate and Significance in the Environment*, Chapter 1, ACS Symposium Series: 459, pp. 2–9, (1991).

Tookey, H.L., et al., "Glucosinolates", *Toxic Constituents of Plant Foodstuffs*, Second Edition, Chapter 4, Edited by Irvin E. Liener, Academic Press, pp. 103–142, (1980).

Traynier, R.M., "Chemostimulation of Oviposition by the Cabbage Root Fly *Erioishia brassicae* (Bouche)", *Nature*, 207, pp. 4992–4993, (Jul. 10, 1965).

Tsao, et al., "Monoterpenoids and Their Synthetic Derivatives", *ACS Symposium Series*, 584, Synthesis and Chemistry of Agrochemicals IV, D.R. Baker et al., eds., American Chemical Society, Washington, D.C., pp. 314–323, (1994).

Tsao, R., et al., "Insecticidal Glucosinolates In Crambe (*Crambe abyssinical*) Seed Extracts", *Picogram and Abstracts*, 45, Abstract No. 49 (Agro), 1 p., (1993).

Tsao, R., et al., "Insecticidal Toxicities of Glucosinolate--Containing Extracts from Crambe Seeds", *J. Agric. Entomol.*, 13 (2), pp. 109–120, (1996).

Tsao, R., et al., "Monoterpenoids and Their Synthetic Derivatives as Leads for New Insect–Control Agents", *Synthesis and Chemistry of Agrochemicals IV*, Chapter 28, ACS Symposium Series: 584, pp. 312–324, (1995).

Tsao, R., et al., "Starting From Nature to Make Better Insecticides", *Chemtech*, 25, pp. 23–28, (Jul. 1995).

VanEtten, C.H., et al., "Natural Sulfur Compounds", *In: Toxicants Occurring Naturally in Foods*, 2nd Edition, National Research Council, National Academy of Sciences, Washington, D.C., pp. 210–234, (1973).

VanEtten, H., et al., "Biological Evaluation of Crambe Seed Meals and Derived Products by Rat Feeding", *Cereal Chem.*, 46, pp. 145–155, (Mar. 1969).

Wadleigh, R.W., et al., "Detoxification of Isothiocyanate Allelochemicals by Glutathione Transferase in Three Lepidopterous Species", *Journal of Chemical Ecology*, 14, pp. 1279–1288, (1988).

Ware, G.W., "Cancelations and Reduced–Use Patterns for Pesticides", *In: The Pesticide Book*, Thomson Publications, Fresno, CA, pp. 222–223, (1994).

Williams, G.M., et al., "Chemical Carcinogens", *Casarett and Doull's Toxicology*, Third Edition, MacMillan Publishing Company, New York, NY, pp. 106–109, (1986).

Wolfson, J.L., "Developmental Responses of *Pieris rapae* and *Spodoptera eridania* to Environmentally Induced Variation in *Brassica nigra*", *Environmental Entomology*, 11, pp. 207–213, (1982).

\* cited by examiner

COMPOUNDS RELATED TO NATURAL SOURCES AND THEIR USE AS BIOPESTICIDES

This application is a continuation-in-part of U.S. application Ser. No. 08/828,190 filed on Mar. 22, 1997, now U.S. Pat. No. 6,207,705 which is hereby incorporated by reference in its entirety.

STATEMENT OF GOVERNMENT RIGHTS

This invention was made with government support under United States Department of Agriculture Grant No. 93-COOP-1-9634 and Hatch funds under project number IOW03187. The United States government has certain rights in this invention.

FIELD

This invention relates to biopesticides, and more particularly to biopesticides that are related to natural sources, including close derivatives and analogs of natural sources.

BACKGROUND

Pesticides are used to increase the world's food supply and decrease disease-carrying pests. However, the large-scale use of pesticides has caused widespread concern regarding environmental impact, increased resistance, as well as acute and chronic toxicity to non-target organisms, including man. Many pesticides, particularly the polychlorinated hydrocarbons such as DDT, have generated much controversy because they persist for years in the environment, and have proven harmful to fish and birds of prey. The concern over the buildup of nondegradable pesticides in the soil and in the food chain has prompted the Federal government to ban the production in the United States of many compounds such as DDT, and severely restrict the use of others.

Two widely used classes of pesticides which decompose more rapidly in the environment than polychlorinated hydrocarbons are the organophosphates and carbamates. Many of these compounds, however, are still considered highly toxic and their use is heavily regulated by the Federal government.

The delivery mechanism, i.e., route of exposure, can be by any means known in the art including, but not limited to, fumigation, contact, dietary or aquatic exposure, and/or any combination of these or other known routes of exposure. One commonly used vehicle for eliminating pests is to fumigate. However, because of the need for high volatility in fumigant use, only about 20 chemicals are routinely used, including compounds containing chlorine, bromine and/or phosphorus. Fumigants may also be used in liquid form for injection into the ground to eliminate pests. There is growing concern, however, that persistence in the soil of certain fumigants is harmful to the environment. As a result, commonly used fumigants such as methyl bromide, dichlorvos, ethylene dibromide, chloropicrin, dibromochloropropane, carbon tetrachloride, phosphine, and 1,3-dichloropropene are heavily regulated and their use is severely restricted.

As part of the Federal government's regulation process, all pesticides must be registered. Since registration can be an extremely time-consuming and very costly process, there has been a marked decrease recently in the registration of new pesticides. This scarcity of new pest control agents has led to concerns that target pests will develop increased resistance to a very limited selection of products. Recently, the government started offering a "fast-track" registration process with the Environmental Protection Agency (EPA) for "biopesticides" which include both naturally-based pesticides and close derivatives or analogs. Although biopesticides offer a desirable alternative to the highly toxic pesticides, relatively few have been registered to date on the fast-track system.

One possible alternative is to use naturally-based pesticides, i.e., "biopesticides." It is well-known that plants have built-in natural defenses against insects and other pests, which have evolved over time. Monoterpenoids, for example, are found in the essential oils of many plants, including mints, pine, cedar, citrus, eucalyptus and spices. Monoterpenoids are known to have the ability to aid plants in chemical defense against insects, bacteria, fungi, and even vertebrate herbivores.

As biopesticides, monoterpenoids have been found to have mild insecticidal activity. The structure-activity relationship of monoterpenoids and monoterpenoid derivatives have been studied, as stated in an abstract entitled, "Insecticidal Properties of Monoterpenoids Against Some Insect Species," Sangkyun Lee, et al., Division of Agrochemical of the American Chemical Society, Fall 1993 and in "Toxicity and Neurotoxic Effects of Monoterpenoids in Insects and Earthworms," Joel R. Coats, et al., Chapter 20, American Chemical Society, 1991, both of which are hereby incorporated by reference.

Many compounds in this class are also used as flavors or fragrances in foods, cosmetics and pharmaceuticals. Further, there are several monoterpenoids that are commercially available for uses such as flea control on pets and carpets, control of insects on house plants, fumigation of parasitic mites in honey bee colonies, and insect repellency, such as with the citronella candle.

Another class of naturally-based pesticides are the glucosinolates. Within the family Cruciferae ("crucifer"), glucosinolates act as natural pesticides in many of the plants. Glucosinolates are a group of over 90 secondary metabolites that occur in only 11 families of dicotyledonous plants, mostly in the family Cruciferae. It has been shown that higher concentrations of glucosinolates correlate with less severe insect attacks. Of interest is the fact that although glucosinolates are reportedly toxic to livestock, they are considered safe for humans. Specifically, within the crucifer family, glucosinolates are found in plants such as cabbages, radishes, turnips, mustard, collard greens, rape, broccoli, kale and crambe (*Crambe abyssinica* L.). It is the breakdown products of glucosinolates which are responsible for the pungent odor and biting taste of these plants.

Studies concerning effects of monoterpenoids and glucosinolates on insect pests have emphasized chemical ecological functions rather than acute toxicity. For example, glucosinolates have been found to play important roles in aiding certain insect species to identify their proper host plants. Experiments have shown that while too low a concentration of glucosinolates leads to ineffective larval attraction, too great a concentration may actually exert a repellent effect to the cabbage root fly. Others have demonstrated that several glucosinolates have a feeding stimulation effect on the diamond-back moth (*Plutella maculipennis* Curtis) and the larvae of *Pieris brassicae*.

Glucosinolate-containing water extracts from crambe meal showing insect. toxicity in laboratory tests are also known and discussed in "Insecticidal Toxicities of Glucosinolate-containing Extracts from Crambe Seeds," by R. Tsao, et al., 1995 which is hereby incorporated by reference in its entirety. The acute toxicity of these extracts as pesticides, however, is significantly lower than conventional organochlorine or organophosphorus pesticides.

There is ongoing debate as to the risks and benefits posed by various natural versus synthetic pesticides. While it is true that many synthetic pesticides are quite toxic, other synthetic pesticides, such as allethrin and methoprene (which are actually biopesticides), are considered relatively safe. Furthermore, although many natural pesticides are relatively safe, there are clearly others, such as nicotine, which are recognized as being quite hazardous. It is now well-accepted that the biological activity of a chemical is a function of its structure rather than its origin, and the biological properties of a chemical depend on this structure as well as the manner in which the chemical is used. The "safety" of a pesticide, therefore, is dependent not only on the chemical make-up of the product, but also on the actual exposure to the chemical. In many cases, the perceived risk is not consistent with the actual risk.

What is needed, therefore, are new types of pesticides or biopesticides to replace those commercial products which are being banned, restricted or phased out, and so that increasing resistance by target pests can be avoided and/or overcome. Further, the replacement pesticides need to be economical, highly toxic to target pests, and pose less actual risk to the environment and humans as compared to traditional pesticides.

SUMMARY

A method for suppressing target pests, comprising exposing the pests to an effective biopesticidal amount of a composition, the composition comprising a carrier and a purified glucosinolate breakdown product having a hydroxyl group attached, wherein a starting material for the purified glucosinolate breakdown product is isolated from a crambe plant or mustard plant, further wherein the target pests are plants, bacteria, fungi or root knot nematodes is disclosed. Methods for suppressing target pests without limitation as to the starting materials are also disclosed wherein the pests are exposed to an effective biopesticidal amount of a composition comprising a carrier and either an analog or a derivative of a purified glucosinolate breakdown product having a hydroxyl group attached. These biopesticides can also be used against plant pests, bacteria, fungi and root knot nematodes.

The present invention provides novel biopesticides that can replace commercial pesticides and biopesticides that have been banned, restricted, or are being phased out, including, but not limited to chloropicrin, dichlorvos and methyl bromide. Many of the biopesticides of the present invention are excellent fumigants, possessing quick action and volatility, while posing less risk than currently used pesticides to humans and the environment.

In one embodiment, the novel biopesticide is a purified form of 4-cyano-3-hydroxy-1-butene (CHB), which is a breakdown product of the principal glucosinolate present in defatted crambe seed meal. Other breakdown products of glucosinolates which have been isolated and purified for use as biopesticides include allyl thiocyanate (ATC), allyl isothiocyanate (AITC) and allyl cyanide (AC).

In a preferred embodiment, an analog of CHB known as 3-cyano-3-hydroxy-1-propene (CHP) is synthesized for use as a biopesticide. CHP is considered a cyanohydrin and has high toxicity or efficacy as a fumigant against pests such as insects and nematodes. Other analogs in the cyanohydrin class are also effective as biopesticides. Examples include the cyanohydrins of simple ketones and aldehydes. Highly effective biopesticides can also be made from isolating the naturally-occurring analogs of CHP which include, but are not limited to dimethyl ketone cyanohydrin (DMK-CNOH) in flax, and methyl ethyl ketone cyanohydrin (MEK-CNOH) in cassava (tapioca).

In an alternative embodiment, derivatives of CHP are produced, including carboxyesters of very small organic acids such as acetic, propionic or propiolic acids. These biopesticides also showed moderate to high efficacy as fumigants.

In yet another alternative embodiment, the derivatives of CHP are carboxyesters made from larger monoterpenoid organic acids such as citronellic acid. These derivatives are essentially "hybrids" of monoterpenoids and cyanohydrins and also show some pesticidal activity.

The biopesticides of natural origin described above, as well as the biopesticides that are close analogs and derivatives of natural biopesticides, will likely be registered as biopesticides through the EPA's fast-track registration channels. Such simplified and rapid registration with the Federal government not only saves time for the producer of the pesticides, but decreases the cost of the final product as well. When waste products from the production of plant oils are used as the starting material, such as with the glucosinolates contained in crambe meal, costs can be reduced even further.

The present invention has application with many target pests including, but not limited to, animal pests such as insects, mites, ticks, nematodes, and plant pests such as weed seeds and weeds commonly found in soils. The present invention can also significantly reduce the number of bacteria and fungi commonly found in soils. Furthermore, different formulations, carriers, or routes of exposure can provide for even further uses for suppression of pests. For example, any of these novel pesticides can be used as fumigants in storage bins, buildings, ships, rail cars, fruit trees and any other products or areas, including storage areas, which are prone to attack by pests. Alternatively, toxicity can be by contact, dietary or aquatic exposure.

BRIEF DESCRIPTION OF THE INVENTION

DETAILED DESCRIPTION OF THE DRAWINGS

Figure 1:
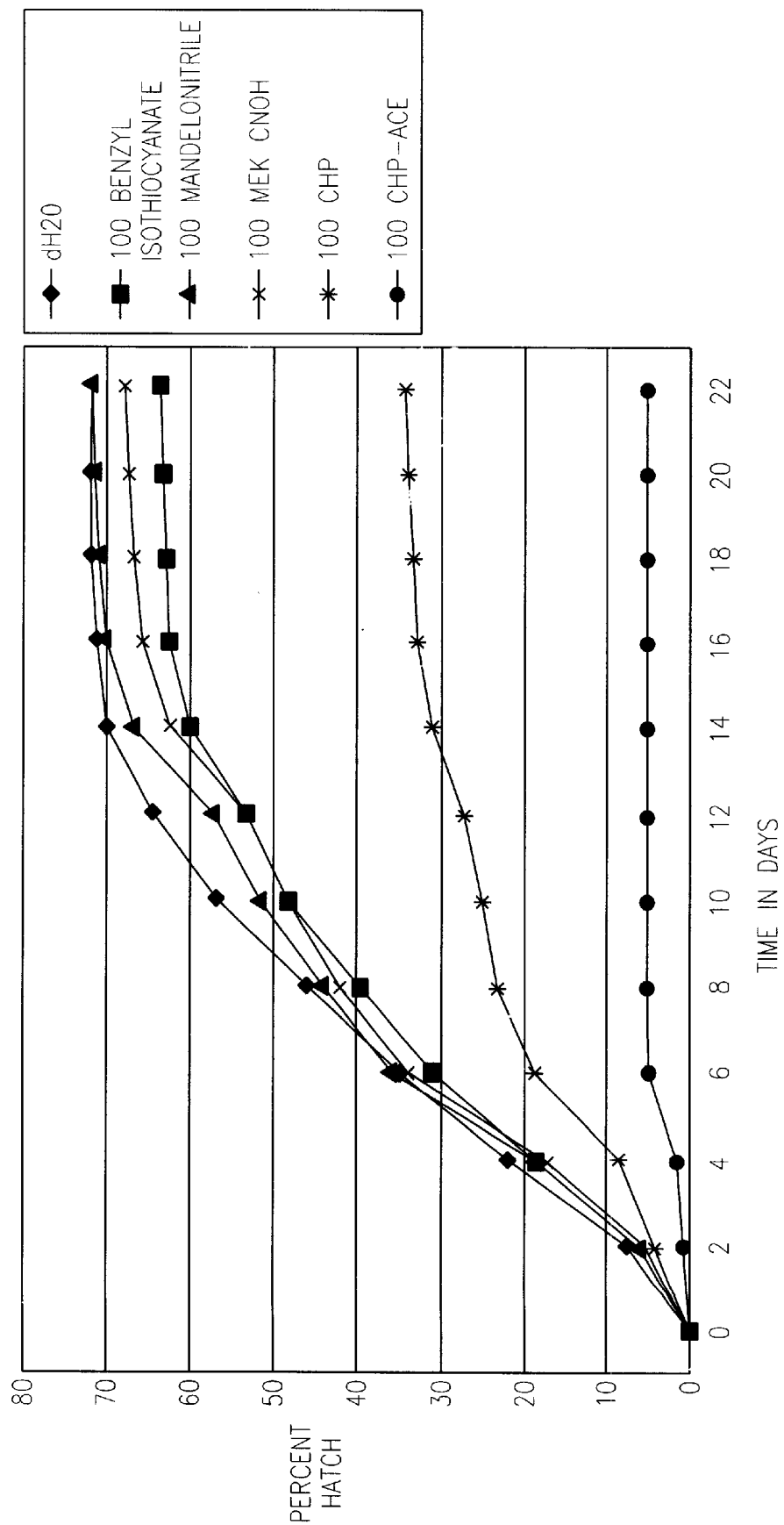
FIG. 1 is a plot of percent hatch versus time for various compounds against root-knot nematode eggs with a contact route of exposure.

The biopesticides of the present invention are related to naturally-occurring breakdown products of glucosinolates, to related analogs and derivatives of glucosinolate breakdown products from any source, and to hybrids comprised of monoterpenoids and particular analogs of the breakdown products. These biopesticides are at least as effective as current biopesticides (e.g., herbicides, fungicides, nematicides, soil sterilants, and so forth) that are being banned or phased out (e.g., methyl bromide, Telone®, etc.), and are less toxic and less harmful to the environment. Various terms used throughout the specification are defined first, followed by a brief discussion of current methyl bromide use. A general overview of glucosinolates and glucosinolate breakdown products is presented next. Discussion of the various embodiments is next, followed by specific examples.

Introductory Definitions

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces. The phrase "closely-related analog" refers to a compound still containing the original toxophore that is present in the parent compound.

The term "bacterium" (singular of bacteria) as used herein refers to the organisms known as "prokaryotes," as distinguished from all other living organisms, which are "eucaryotic." Since bacteria are distinct from other living organisms, they are classified in their own kingdom, Monera. Bacteria are metabolically diverse, with some being photo synthetic. There are literally thousands of species of bacteria, with many being beneficial to other living organisms. However, some types of bacteria, i.e., pathogenic bacteria, are known to cause a number of different diseases in plants and animals. Generally, pesticide use intended for bacteria is directed towards pathogenic bacteria. Almost all kinds of plants can be affected by bacterial disease. Virtually all plant-pathogenic bacteria are bacilli, and most, but not all, occur primarily in their host plants as parasites. Example genera (and diseases) include, but are certainly not limited to, Agrobacterium (crown gall, twig gall, cane gall, hairy root), Corynebacterium (potato ring rot, tomato canker and wilt, fruit spot, fasciation), Erwinia (blight, wilt, soft rot), Pseudomonas (leaf spots, canker and bud blast, banana wilt, olive galls, lilac blight) Xanthomonas (leaf spots, black venation, cutting rot, bulb rot, citrus canker, walnut blight), Rizobium (root nodules of legumes), Streptomyces (potato scab), and so forth.

The term "carrier" as used herein refers to the means by which the toxophore in the biopesticide is delivered to the target pest, the means by which the target pest is exposed to the biopesticide. A carrier can include, but is not limited to, oils, including any type of vegetable oils, such as canola oil, soybean oil, and so forth, polymers, plastics, waxes, wood, gels, colloids, granular materials, such as clays and minerals (e.g., vermiculite, bentonite), dusts, powders, baits, sprays, drenching means, emulsifiable concentrates, and so forth. The choice of delivery means depends on several factors, including, but not limited to, the specific need, the toxicity of the pesticidal agent itself, and so forth.

The term "derivative" as used herein refers to a chemical substance related structurally to another, i.e., an "original" substance, which can be referred to as a "parent" compound. As such, some monoterpenoids can be considered to be derivatives of monoterpenes or in some cases may be derivatives of other monoterpenoids. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

The term "fumigation" as used herein refers to the use of a gas pesticide, or a volatile solid or liquid pesticide to control pests in storage bins, buildings, ships, rail cars, stored products, soil, on foods, plants, other living organisms, or in any closed areas which are prone to attack by pests, i.e., pest infestation.

The term "fungus" as used herein refers to any of a major group (Fungi) of saprophytic and parasitic lower plants without chlorophyll that include true fungi, molds, rusts, mildews, smuts and mushrooms.

The term "monoterpene" as used herein, refers to a compound having a 10-carbon skeleton with non-linear branches. A monoterpene technically refers to a compound with two isoprene units connected in a head-to-end manner. The term "monoterpenoid" refers to a monoterpene-like substance and may be used loosely herein to refer collectively to monoterpenoid derivatives as well as monoterpenoid analogs. Monoterpenoids can therefore include monoterpenes, alcohols, ketones, aldehydes, ethers, acids, hydrocarbons without an oxygen functional group, and so forth. It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein.

The term "pest" as used herein refers to a plant, animal, bacteria or fungus detrimental to man. The phrase "parasitic pest" refers to a pest that lives on or in another living organism to the detriment of that organism.

The term "pesticide" as used herein refers to an agent that destroys pests. The term "biopesticide" refers to a pesticide derived from natural sources. Biopesticides also include "close" synthesized derivatives and analogs of biopesticides. Although the terms "biopesticide" and "pesticide" may be used interchangeably herein, a biopesticide is technically not considered to include a synthetic pesticide that is not a close derivative or analog. The term "herbicide" refers to an agent used to destroy or inhibit plant growth. Similarly, the term "fungicide" refers to an agent that destroys fungi or inhibits their growth. The term "nematicide" refers to an agent that destroys or inhibits nematode or nematode egg growth. The term "bactericide" refers to an agent that destroys or inhibits bacterial growth. The term "soil sterilant" refers to an agent used to suppress or inhibit pathogenic microorganisms in the soil, but does not necessarily imply total sterilization of the soil, nor does it imply that the effects are permanent. Therefore, herbicides, fungicides, nematicides, bactericides, and so forth, as well as soil sterilants, can all be considered types of "pesticides."

The term "plants" as used herein refers primarily to chlorophyll-containing plants, including, but not limited to, chrysophytes, green algae, brown algae, red algae, bryophytes, tracheophytes.

The term "soil fumigant" as used herein refers to a pesticide that is applied directly into the soil. A pesticide classified and labeled as a soil fumigant means that it can control nematodes, insects, pathogenic soil fungi and bacteria, as well as weed germination.

The term "suppress" as used herein means to reduce or limit the incidence or severity of a pest infestation or pest activity, even if for a limited period of time.

Current Methyl Bromide Use

Methyl bromide is the second most widely applied pesticide in the world and is the fifth most widely-used pesticide in the United States. Methyl bromide is typically used as a soil fumigant (80%) and is also used as a fumigant for agricultural commodities in food and packaging materials and facilities (15%). Methyl bromide is known to kill insects, nematodes, microorganisms, weeds, including germinating weed seeds, rodents and other pests. With such a wide spectrum of bioactivity, it is often referred to as a "soil sterilant," although the sterilizing effects typically last only a short time. However, growers of strawberries, tomatoes, tobacco, peppers, grapes, nuts, and many other crops, often rely on this initial "knockdown" of all pests to get their crops off to good starts. Methyl bromide is also used in post-harvest pest control for products such as grapes, raisins, cherries and nuts. Methyl bromide is also known to be effective against pest infestations in buildings, such as warehouses and mills for processing grain. Further, many imported and exported agricultural products must be treated because of regulations in various countries, including the United States.

However, of the 80% of methyl bromide that is field applied, large amounts have been shown to volatilize into the atmosphere. In fact, methyl bromide is a major contributor to the destruction of the ozone layer, as it is considered to be the primary source of bromine radicals in the stratosphere. Specifically, bromine radicals are known to scavenge ozone forty times more effectively than chloro-fluorinated hydrocarbons. As a result, the standards set by the 1990 Amendments to the Clean Air Act mandated the phasing out of methyl bromide by 2001. However, due to the lack of suitable alternatives, the 1998 Amendment to the Agriculture Bill slowed the phasing out of methyl bromide to 2005, starting with a 25% reduction in 1999.

Although some alternatives are currently available, most are not as effective as methyl bromide, are suitable only for certain pests or crops, and/or are very expensive. Many alternatives also have known negative health and environmental effects, with many currently being phased out. These include, but are not limited to Telone®, chloropicrin, ethylene dibromide, dibromochloropropane and metam sodium. (Telone® is made by Dow Chemical in Midland, Michigan and contains the compound 1,3-dichloropropene). Non-chemical alternatives, such as controlled atmospheres of carbon dioxide or nitrogen, heat, cold, steam, changes in agricultural practices, improved plant varieties, and so forth, need to be further developed before they can be considered practical alternatives to methyl bromide.

Glucosinolates and Glucosinolate Breakdown Products

A glucosinolate molecule consists of three parts: a glucose, a sulfate, and a toxophore containing an elemental sulfur atom. The toxophore or aglycone is the toxic portion of the molecule which is the organic group that remains after the glucose, sulfate, and sometimes the elemental sulfur are hydrolyzed off the glucosinolate molecule. This toxophore is also referred to as a glucosinolate breakdown product. The general structure of a glucosinolate molecule is:

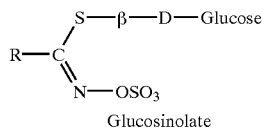
Glucosinolate

The glucosinolate breakdown products fall into three general classes of compounds: nitrites, thiocyanates, and isothiocyanates as shown below:

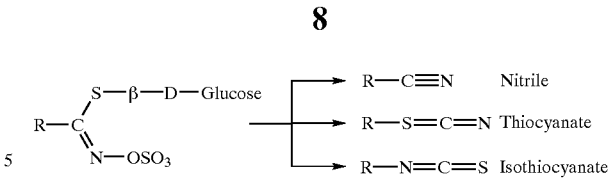

Glucosinolates are prevalent in the crambe plant. Crambe is a cruciferous plant, which is a potentially important oil crop in the Midwest of the United States. The seed oil of crambe can be used as an industrial oil or for human nutrition. The remaining defatted seed meal can be used as a protein source in livestock diets. However, because the high concentrations of glucosinolates and their breakdown products in the meal are toxic to the livestock, the glucosinolates must be removed or extracted from the meal before use as livestock feed. Thus, any use of these extracts would be of great advantage in terms of recycling our natural resources.

Although other sources of glucosinolates can be used as the starting material in the present invention, preferably crambe meal is used because it is readily available as a low cost by-product from the production of oil as noted above. Alternative sources of glucosinolates include rapeseed and black mustard.

Two of the glucosinolates in crambe seed meal are epi-progoitrin and sinigrin. The major glucosinolate is epi-progoitrin having a chemical structure as shown below:

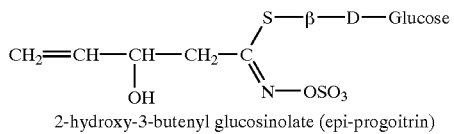
2-hydroxy-3-butenyl glucosinolate (epi-progoitrin)

In crambe meal, epi-progoitrin breaks down into two products, namely the S-enantiomer of 1-cyano-2-hydroxy-3-butene (CHB) and goitrin. CHB has the following formula:

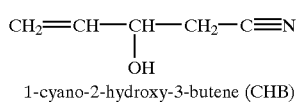
1-cyano-2-hydroxy-3-butene (CHB)

Goitrin has the formula:

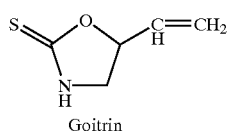
Goitrin

Sinigrin, another glucosinolate in crambe seed meal, has a chemical structure as shown below:

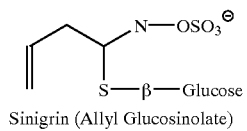
Sinigrin (Allyl Glucosinolate)

Sinigrin breaks down into a number of products including allyl thiocyanate (ATC), allyl isothiocyanate (AITC), and allyl cyanide (AC), having the following chemical formulas:

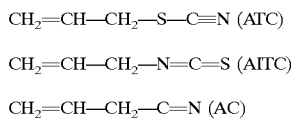

Discussion of Various Embodiments

In one embodiment of the present invention, CHB is isolated and purified from any naturally-occurring source by any suitable method. In a preferred embodiment, crambe meal is used as the source of CHB for the reasons noted above. In an alternative embodiment, rapeseed meal can be used as a source of CHB after the oil has been removed. The use of rapeseed meal, however, results in the R-enantiomer rather than the S-enantiomer as with crambe meal. Although both can display insecticidal activity, the comparative insecticidal potency of the two enantiomers is unknown.

Preferably, CHB is isolated by first treating the glucosinolate source, such as crambe meal, with water or a mineral acid such as dilute sulfuric or dilute nitric acid. The resulting intermediate can then be extracted with a suitable solvent by an appropriate extraction technique, but is preferably extracted using direct extraction for a suitable time period, such as about four (4) to about twenty-four (24) hours. The solvent is preferably one which is moderately lipophilic and not miscible with water, such as methylene chloride, ethyl acetate, chloroform, diethyl ether, and carbon tetrachloride.

The isolated agent (CHB) is then concentrated and purified by any suitable method. In one embodiment, concentration and purification are achieved by rotary evaporation and open-column chromatography on silica gel. Any suitable method can be used to determine the purity of the fractions, including, but not limited to thin-layer chromatography.

A purified glucosinolate breakdown product according to the present invention comprises a composition having at least five (5)% by weight of a glucosinolate breakdown product (such as CHB), as a glucosinolate breakdown product occurs in nature in lesser concentrations. It is preferred that the purified product contain at least 10% or at least 20% of a glucosinolate breakdown product. In a more preferred embodiment, the purified product contains at least 30% or at least 40% by weight of a glucosinolate breakdown product. Most preferably the final product contains at least 50%, at least 60%, at least 70%, at least 80%, at least 90%, or even 100% by weight of a glucosinolate breakdown product.

In one embodiment, as shown in Example 1, dilute hydrochloric acid is used to isolate the CHB by refluxing crambe meal for about 24 hours with dichloromethane. Continuous direct extraction of the CHB in a Soxhlet apparatus is used which produces a relatively high yield of CHB, in the range of about 0.15%. A Soxhlet apparatus is a continuous extraction apparatus which can be used to extract organic substances from plant or animal matter.

The results in Example 1 indicate that isolated and purified CHB has only marginal usefulness as a pesticide fumigant, as it demonstrated only mild vapor toxicity and topical toxicity. Isolated and purified CHB may be more effective as a pesticide, however, if delivered in bait form. Further results from specific testing with nematodes, as described in Example 6, show that isolated and purified CHB inhibit the hatch of soybean cyst nematode eggs very effectively.

ATC and AITC and AC (the active breakdown products of sinigrin) were also tested as pesticides as shown in Example 1, and demonstrate moderate to highly effective fumigant activity. Again, any suitable source of these breakdown products can be used. In a preferred embodiment, however, AC and AITC are obtained from an outside source as a pure chemical because it only occurs in crambe seed meal in low concentrations. ATC also occurs in crambe seed meal in low concentrations, but is preferably synthesized in the lab, as shown in Example 1, because it is more economical.

In another embodiment, an analog of CHB known as 3-cyano-3-hydroxy-1-propene (CHP) can be synthesized for use as a pesticide. CHP has one less carbon atom than the naturally-occurring CHB and also has the cyano and hydroxy functional groups on the number '3' carbon. This is as compared with CHB, which has these groups on different carbons, namely the '3' and '4' carbons. Therefore, CHP is technically a member of a class of compounds called cyanohydrins, since the cyano and hydroxy functional groups are both attached to the same carbon. Although cyanohydrins are known to be naturally occurring (such as the mandelonitrile found in the pits of peaches and related drupes), CHP itself is not known to be naturally occurring. As shown below in Example 2, CHP is a very effective fumigant against insects and likely other pests including, but not limited to, nematodes. CHP can also likely be used by other routes of exposure including, but not limited to aquatic and topical application.

In another embodiment, other analogs in the cyanohydrin class can be synthesized for use as pesticides, including the cyanohydrins of simple ketones and aldehydes. As stated above, the analogs herein include compounds which still contain the original toxophore, but have had either an entire organic group of the parent compound (such as a methyl group) substituted with a different group (such as an ethyl, halogen, amino carboxyl, vinyl, ethynyl, allyl, alkoxy, alkyl, or allylthio group), or an entire organic group of the parent compound removed (such as with CHP when a methylene group was removed from CHB), or have had one or more hydrogen atoms either removed (to yield an ethylene bond) or replaced with other groups such as halogen, carboxy, or carbonyl group). As Example 3 shows, these compounds have high toxicity as fumigants. Although only these particular analogs were tested, it is likely other analogs in the cyanohydrin class are also excellent pesticides including. These include, but are not limited to those aldehydes and ketones from which cyanohydrins can be made having a relatively low molecular weight of about 80 amu or less. Examples of such compounds include, but are not limited to, diethyl ketone, isobutyraldehyde, propionaldehyde, cyclobutanone, fluoroacetone and di-tert-butyl ketone. The naturally-occurring analogs of CHP, such as DMK-CNOH found in flax and MEK-CNOH found in flax and cassava are also excellent pesticides and have all of the advantages of a pesticide derived from a natural source.

In another embodiment, derivatives of CHP are synthesized, including carboxyesters of very small organic acids, such as acetic, propionic, propiolic, pivalic, chloroacetic, and chloropropionic. These small volatile cyanohydrin derivatives, which can be referred to generally as CHP with organic ester substituents of less than three (3) carbon atoms are highly toxic to insects and likely to many other pests as well, as shown in Example 4.

In yet another embodiment, other derivatives of CHP include carboxyesters (such as citronellic acid and geranoic acid) made from larger monoterpenoid carboxylic acids are synthesized. Although these derivatives are much larger than those described in Example 4, they are still considered close derivatives to the parent compound as the molecular weights of these derivatives do not exceed 50% above the molecular weight of the parent compound. As stated above, a monoterpenoid is a monoterpene-like 10-carbon compound composed of two isoprene units connected in a head-to-end manner. Modifying the functional groups of monoterpenoids for use as pesticides is advantageous for several reasons. Derivatization can increase toxicity at the active site in an insect's body, increase lipophilicity and delivery into the insect body, and/or increase stability. The synthesized compounds, which are essentially "hybrids" of monoterpenoids and cyanohydrins were also tested for use as pesticides, as shown in Example 5. The results indicate that these hybrids have some pesticidal activity.

In yet another embodiment, many of the derivatives and analogs of CBP, as well as CHB are synthesized for nematicidal use as shown in Examples 6 and 7, and function as highly effective nematicides.

In another embodiment, many of the derivatives and analogs have demonstrated usefulness as fungicides, soil sterilants and herbicides as shown in Example 8.

In another embodiment, additional methods that can be used to test biopesticides in order to determine the antimicrobial activity in soil and to determine the inhibition of seed germination or toxicity to germinating weeds are discussed in Example 9.

Even greater toxicity effects can be achieved by adding known toxophores or toxic groups from other classes onto the core structures of the present invention or even dimerizing the core structure of the parent compound which could reduce mobility of the molecule.

The compositions of the present invention comprise the biopesticide together with a suitable carrier. These compositions are effective against a variety of pests, as noted, including plant pathogens. Plant pathogens include both bacteria and fungus, as well as viruses and mycoplasma-like organisms, non-parasitic diseases and mycorrhizas. Such pathogens are too numerous to itemize, but include, at a minimum, the pathogens listed in the journals entitled, "Review of Plant Pathology," ISSN: 0034–6438, Volumes 70–79, CABI Publishing, New York, N.Y. (1990–2000), which are all hereby incorporated by reference in their entirety. (These journals are also available as a searchable dataset on the Internet through CABI's PEST CABWEB® service. See also http://www.cabi.org).

The invention will be further described by reference to the following examples which are offered to further illustrate various embodiments of the present invention. It should be understood, however, that many variations and modifications may be made while remaining within the scope of the present invention.

EXAMPLE 1

Crambe Extracts and Purifief Glucosinolate Breakdown Products as Pesticides

I. Background

Seven compounds were tested as pesticides in this study: Allyl cyanide (AC), allyl isothiocyanate (AITC), and allyl thiocyanate (ATC), which are the major breakdown products from sinigrin; 1-cyano-2-hydroxy-3-butene (CHB), and goitrin, the major breakdown products from epi-progoitrin; crude extracts of *C. abyssinica* seed meal; and the ground seed meal itself.

Two standard pesticides, dichlorvos and chloropicrin, were also included in this study to provide a comparison for the fumigation assays. These standards were obtained from Chem Service of West Chester, Pa. Dichlorvos has been banned for many uses, including fumigation, and the use of chloropicrin is also. heavily restricted. These two chemicals were chosen as standards, however, because they are two of the most potent fumigants ever used. Methyl bromide, however, has been the most widely used fumigant for decades. It is used exclusively as a fumigant, and is the second-most used insecticide in the world. It is known that chloropicrin is slightly more effective than methyl bromide as a fumigant against five stored products pests (i.e., the granary weevil, the drugstore beetle, the confused flour beetle, the bean weevil, and the saw-toothed grain beetle), having $LC_{50}$ values in the range of from less than about 1.5 to about 6.4 mg/L as compared with about 4.2 to about 9.2 mg/L for methyl bromide. Methyl bromide was not selected as a standard because it has a boiling point of 38° F., and is hard to handle except under pressure or in very cold vessels as it is a gas at room temperature.

Where possible, the experimental compound was tested against one or two standards. If the experimental compound was at least as good or better than a particular standard, it can be considered a highly effective fumigant. If the $LC_{50}$ is two to five times higher than the standard, it is likely a moderately effective fumigant. If the compound has an $LC_{50}$ greater than five times higher than the standard, it is considered to be a relatively weak fumigant. All $^1H$ NMR spectra were obtained in deuterochloroform on a Varian VXR 300. An infrared spectrum of allyl thiocyanate was obtained using a Beckman Acculab 2 on NaCl plates, the sample being dissolved in dichloromethane. An infrared spectrum of CHB was obtained on the same apparatus, but by placing a drop of pure sample on a 3M Type 61 Disposable IR card.

II. Starting Materials

A) Allyl Cyanide (AC) and Allyl Isothiocyanate (AITC) and Goitrin AC and AITC were obtained from the Aldrich Chemical Co. in Milwaukee, Wis. Five (5) grams of AC was purchased, at 98% purity. Five (5) grams of AITC was purchased, at 95% purity. Both were dissolved in acetone as stock solutions for making serial dilutions for toxicity testing.

The goitrin was also dissolved in acetone as a stock solution for making serial dilutions for toxicity testing. Goitrin was purchased from Lancaster Chemical Co. In Windham, N.H. Approximately 50 mg of goitrin was purchased, at about 98% purity.

B) Synthesis of Allyl Thiocyanate (ATC)

The sinigrin aglucone allyl thiocyanate was synthesized through the action of allyl chloride and potassium thiocyanate, in a reaction procedure modified from various techniques in Furniss, et al. (1989).

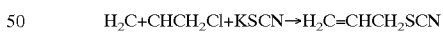

Two hundred ml of dimethyl sulfoxide (DMSO) was put into a large flask and 30 g (0.31 mol) KSCN was added. The mixture was heated to 85° C. on a water bath. The water bath was removed and 24.5 ml (0.30 mol) allyl chloride was added slowly. The reaction mixture was allowed to cool and was then washed with four 200 ml portions of anhydrous diethyl ether. An ethereal layer was passed over sodium sulfate (to remove water) and the ether was removed with a rotary evaporator at 20 in. Hg vacuum at 25° C. The resulting product was purified using open-column chromatography on silica gel using 10:2 hexane:diethyl ether, collected in 25 ml portions. Like portions were combined and brought to dryness on a rotary evaporator at the above-mentioned conditions. Observed infrared spectra shown in Table 1 agrees with that expected based on Silverstein, et al. (1991).

TABLE 1

Observed infrared spectra of allyl thiocyanate compared to expected peaks

| Group | Observed cm$^{-1}$ | Expected cm$^{-1}$ |
|---|---|---|
| C—H alkene | 3050 | 3049 |
| C—H alkane | 2960–2880 | 2960–2850 |
| SCN | 2160 | 2200–2000 |
| C=C | 1635 | 1640 |

$^1$H NMR of the synthetic product agrees with that expected from Silverstein, et al. (1991).

TABLE 2

Observed NMR spectra compared to the spectra expected for allyl thiocyanate

| Observed Peaks | Expected Peaks |
|---|---|
| 5.8–6.0 (m) 1 H | 6.50 1 H |
| 5.4–5.3 (m) 2 H | 5.20 2 H |
| 3.55 (d) 2 H | |

C) Extraction of (S)-1-cyano-2-hydroxy-3-butene (CMP)

(S)-1-cyano-2-hydroxy-3-butene (CHB), the nitrile aglucone of epi-progoitrin, was isolated through Soxhlet extraction of defatted seed meal of crambe. One hundred grams of crambe meal from the Iowa State University Center for Crops Utilization in Ames, Iowa was placed in the Soxhlet apparatus and 500 ml dichloromethane was allowed to cycle through the apparatus for 24 h at 45° C. The collected dichloromethane was reduced to 50 ml on a rotary evaporator at 20 in. Hg vacuum at 25° C. The organic solution was extracted with three volumes of water, and the water layer was extracted three volumes of diethyl ether. The ether portions were brought to dryness on a rotary evaporator at the conditions mentioned above. The resulting product was purified using open-column chromatography on silica gel and a 4:6 hexane:diethyl ether solvent system, collected in 25 ml portions. Like portions were combined and brought to dryness on a rotary evaporator at the above-mentioned conditions. Infrared spectroscopy (IR) of the isolated CHB agreed with that published in Daxenbichler, et al. (1968) and agrees with that expected based on Bellamy (1959) as shown in Table 3.

TABLE 3

Comparison of observed and published and expected IR peaks of CHB

| Group | Observed cm$^{-1}$ | Published cm$^{-1}$ | Expected cm$^{-1}$ |
|---|---|---|---|
| O—H | 3600–3200 | 3400 | 3650–3590 |
| C—H alkene | 3150 | bands reported | 3100–3077, 3025–3010 |
| C—H alkane | 2930 | bands reported | 2930–2850 |
| CN | 2270 | 2260 | 2260–2240 |
| C=C (vinyl) | 1640 | 1680–1620 | |

$^1$H NMR peaks agreed with those published in Das and Torssell (1983) and agreed reasonably well with those expected based on Silverstein, et al. (1991) as shown in Table 4.

TABLE 4

Observed chemical shifts compared with those published and those predicted for CHB

| Observed Peaks | Published Peaks | Expected Peaks |
|---|---|---|
| 2.65 (m) 2 H | 2.60 (d) 2 H | 2.20 1 H |
| 2.80 (br.s.) 1 H | 4.0 (br.s.) 1 H | 2.40 1 H |
| 4.45 (m) 1 H | 4.40 (q) 1 H | 4.38 1 H |
| 5.3 (d) 1 H | | 5.20 2 H |
| 5.45 (d) 1 H | | 5.1–6.2 (m) 3 H |
| 5.90 (m) 1 H | | 6.50 1 H |

With use of the isolation and purification method described in this Example, the final product had a composition of approximately 95% by weight of CHB. It is likely that even higher purity levels can be achieved using other suitable methods of isolating and purifying CHB.

D) Preparation of Crude Extracts from Crambe Seed Meal

Crude extracts were prepared by soaking 100 g seed meal in 500 ml of 50% methanol, 50% ethanol, 50% acetone or 100% water for 24 h, followed by removal of the meal by filtration and condensation to 100 ml on a flash evaporator. The 100 ml was considered to be the stock solution and all dilutions are in reference to this stock.

III Test Organism and Assays

Table 5 shows which chemicals were tested on the various organisms, and the method by which they were tested.

TABLE 5

Organisms and Assays

| Organism - Common Name | Assay | Chemical |
|---|---|---|
| House fly (adult) | Fumigation | AC, ATC, AITC, CHB |
| | Topical | Goitrin, CHB, AITC, AC, ATC |
| Lesser grain borer | Fumigation | AC, ATC, AITC, CHB |
| House fly (larvae) | Larval medium | C. abyssinica seed meal |
| Western corn rootworm | Soil assay | ETOH, MEOH, Acetone and Water extracts |
| Yellow fever mosquito (larvae) | Aquatic assay | ETOH, MEOH, Acetone and Water extracts AC, ATC, AITC, CHB |
| Brine shrimp | Aquatic assay | AC, ATC, AITC, CHB |

IV. Test Producers

A) Fumigation Assay Procedures

House Fly (Adult) (*Musca domestica*)

Approximately 10 adult flies were anesthetized with $CO_2$ and placed into a 50 ml jar supplied with dry food (1:1 sucrose:dehydrated milk) and a two (2) cm length of cotton roll wetted with distilled water. The jar was covered with a square of nylon mesh (wedding veil) and secured with a rubber band. After the flies recovered from anesthesia, three of the small jars were placed into a large 2745 ml amber jar. A piece of Whitman #4 filter paper was folded in quarters and placed in the bottom of the amber jar with the flies. To the filter paper was applied 200 µl of the appropriate corn oil dilution. The jar was securely capped and left undisturbed for the appropriate time period. The jars were opened and the mortalities recorded after 24 h. The flies were considered dead when they displayed no observable response (e.g. wing or leg movements) to outside stimuli, such as prodding.

Lesser Grain Borer (*Rhizopertha dominica*)

The lesser grain borer is a beetle that bores into and feeds on stored grain. Precisely ten (10) adult beetles were placed in a 1.5×4.0 cm tube fitted with a metal screen secured by parafilm, leaving an area open to allow gas exchange.

Approximately one (1) g of whole wheat kernels was placed in the tube before the introduction of insects. The open end of the tube was closed with a metal screen secured with parafilm, leaving an open area to allow for gas exchange. Three tubes were fastened together and suspended in a 490 ml (1 pt.) mason jar. A piece of Whatman #4 filter paper was folded into quarters and placed in the bottom of the jar. To the filter paper was applied 100 µl of the appropriate corn oil dilution. The mason jars were securely capped and left undisturbed for the appropriate time period. The jars were opened and the mortalities were recorded after 24 h. Since this species feigns death, the beetles were considered dead when they displayed no observable response (e.g. leg or antennal movements) to outside stimuli for >30 s.

B) Larval Medium Procedure

House Fly (larvae) (*Musca domestica* L.)

Larval medium experiments involved incorporating raw defatted crambe meal into the laboratory medium for housefly larvae in a 1:1 ratio or rearing the larvae in crambe meal alone.

C) Soil Assay Procedure

Western corn rootworm (*Diabrotica virgifera*)

The bioassay of the western corn rootworm followed the procedure in R. Tsao, et al., supra, 112. Fifty grams of autoclaved soil (sandy clay loam soil, collected in a pesticide-free field, Ames, Iowa, with 50% sand, 26% silt, 22% clay, 2.3% organic matter, pH 5.3) was placed in a Petri dish (10-cm diam) and moistened with 12 ml of water for control and aqueous solutions of crambe extracts for the treatments. Five corn seedlings (3–4 cm long) were arranged in a circle on top of the soil, followed by the introduction of 10 western corn rootworm larvae (3rd instar, aged 10–13 d) in the center of the dish. The treated Petri dishes then were put in an incubator at 25±1° C., relative humidity 45±5%, and a photo period of 12:12 (L:D) h. The experiment was carried out in duplicate. Mortalities were recorded after 24 h and 48 h. Larvae that were not able to move were regarded as dead.

D) Aquatic Assay Procedures

Yellow fiver mosquito (larvae) (*Aedes aegypti*)

The bioassay of the yellow fever mosquito was carried out following the procedure in R.Tsao, et al., supra, 111–112. Ten mosquito larvae (early 2nd instar) were exposed to 20 ml of differently diluted extracts (with distilled water) in a 50-ml jar. Other treatments included 0.5 ml of acetone solutions of AC, ATC, AITC and CHB which were added to the jars that held the 20 ml of distilled water. The larvae were transferred to the jar one (1) hour later, carefully with an eye-dropper. The treated jars were kept in an incubator at 25±1° C. in the dark and with relative humidity of 45±5%. The larvae were given a small amount (approximately 0.1 g) of food (ground Waywardly, Tropical Flakes fish food, Waywardly Laboratories, Inc., Secaucus, N.J.). The test was done in three replicates. Mortality was recorded 24 h post treatment. Larvae that were not able to swim were regarded as dead.

Brine shrimp larvae (*Artemia franciscana*)

The same procedure as for the yellow fever mosquito larvae was performed using the same extracts. In this experiment about 50–60 brine shrimp larvae were used per test. Brine shrimp larvae are typically used as aquatic test species because they are inexpensive, readily available at anytime, and they react similarly to various aquatic pests, such as larvae of mosquitoes, black flies and midges. Specifically, they are commercially available as dried cysts which can be stored for months and will hatch quickly in aerated water.

E) Topical Application

Acute topical toxicities against the adult house fly were carried out according to "Insecticidal Properties of Several Monoterpenoids" by Rice, et al., 1172, 1173, Journal of Economic Entomology, Vol. 87, no. 5 (1994), which is hereby incorporated by reference. Instead of delivering monoterpenoids with an electric micro applicator, however, glucosinolate breakdown products were instead delivered.

As described in Rice et al., acute topical toxicity was examined with adult *M domestica* (10 d after eclosion, susceptible strain; Orlando regular). An electric micro applicator delivered 1 µl of each of the glucosinolate breakdown products in acetone in the pronota of anesthetized ($CO_2$ and ice) flies. Initial studies were conducted to determine appropriate ranges of testing concentrations. Technical grade chlorpyrifos (Dow-Elanco, Midland, Mich.) and 20% (AI) pyrethrins (Pet, Miami Springs, Fla.) served as the standards for comparison. Certified acetone was used as the control treatment. A minimum of four concentrations (micrograms per insect, based on range-finding results) were replicated at least three times (10 flies per replication) for the final bioassays. Mortality was assessed 24 h after treatment. The trimmed Spearman-Karber method (Hamilton et al. 1977) was used to estimate $LC_{50}s$.

The control treatment was acetone solvent. Dichlorvos was used as the new standard.

V. Results

A) Fumigation Assays

1) Adult Housefly

Table 6 shows the results of the fumigation studies with AC, ATC, AITC, and CHB as compared with two standard pesticides, dichlorvos and chloropicrin.

TABLE 6

Fumigation toxicities of sinigrin and epi-progoitrin breakdown products against adult housefly (*M. domestica*) after 24 h

| Compound | $LC_{50}$ ($\mu g/cm^3$)[a] | 95% FL[b] |
|---|---|---|
| Dichlorvos (standard) | <0.008 | |
| Chloropicrin (standard) | 0.08 | 0.076, 0.099 |
| ATC | 0.1 | 0.08, 0.12 |
| AITC | 0.13 | 0.10, 0.16 |
| AC | 3.66 | 3.11, 4.10 |
| CHB | 6.2 | 4.91, 9.73 |

[a]$LC_{50}$ is the concentration ($\mu g/cm^3$) of chemical that is required in the container to cause lethality to 50% of the test insects in 24 h. (SAS Institute (1991).
[b]95% Fiducial limits are the 95% confidence intervals, i.e. the range of values within which one can be 95% certain that the $LC_{50}$ would fall if the test were to be repeated (SAS Institute (1991).

Table 6 shows that two of the sinigrin breakdown products (ATC and AITC) are highly effective fumigants, as they were nearly as good as the chloropicrin fumigant. AC was a relatively weak fumigant, having about 46 times less toxicity than chloropicrin. The isolated and purified CHB (epi-progoitrin breakdown product), was also a relatively weak fumigant against the adult housefly, having approximately 77 times less toxicity than chloropicrin.

2) Lesser Grain Borer

The fumigation toxicities of sinigrin and epi-progoitrin breakdown products against the lesser grain borer are shown in Table 7.

TABLE 7

Fumigation toxicities of sinigrin and epi-progoitrin breakdown products against the lesser grain borer (*R. dominica*) after 24 h

| Compound | $LC_{50}$ ($\mu g/cm^3$) | 95% FL |
|---|---|---|
| Dichlorvos (standard) | 0.29 | 0.21, 0.41 |
| ATC | 0.37 | 0.14, 0.42 |
| Chloropicrin (standard) | 1.3 | 1.20, 1.42 |
| AITC | 1.57 | 1.47, 1.67 |
| AC | 2.8 | 2.26, 3.48 |
| CHB | >19.60 | |

The results show that the three allyl compounds of sinigrin (ATC, AITC and AC) controlled the lesser grain borer about as well as the two standards, and therefore are highly effective fumigants. CHB, however, required a concentration greater than 19.6 $\mu g/cm^3$ to kill 50% of the beetles, as compared to 0.29 to 2.8 $\mu g/cm^3$ for the two standards. As CHB was about 68 to 70 times less effective than dichlorvos and chloropicrin, respectively, it is considered a relatively weak fumigant.

B) Larval Medium Assay
1) House Fly (Larvae)

Table 8 shows the effect of the crude extract of crambe meal on the house fly larvae after 15 days.

TABLE 8

Toxicity of crude water extract of crambe meal on the house fly larvae (*M. domestica*) after 15 days

| % meal in diet | % mortality |
|---|---|
| 100 | 90 |
| 50 | 80 |
| 0 | 10 |

Although no standard was tested in this experiment, permethrin, which is considered an effective pesticide in a larvae medium assay, has roughly 98% mortality when there is about one (1) % pesticide in the diet. The results in Table 4 indicate that crude crambe meal is only slightly toxic to housefly larvae when incorporated into their diet. The 100% replacement of the house fly medium resulted in 90% mortality of the larval flies, while replacement of 50% of their medium with crambe meal controlled 80% of the fly larvae. This confirms previous work in the industry, showing that as a pesticide, the crude water extract of crambe meal does not possess significant toxicity to warrant consideration as a replacement pesticide through a bait exposure.

C) Soil Assay
1) Western Corn Rootworm

Table 9 shows the toxicity of the various extracts of crambe meal to western corn rootworm in a 24 hour period.

TABLE 9

Toxicities of various extracts of crambe meal to western corn rootworm (*Diabrotica virgifera*) (Percent mortality at 24 h)

| Extract | 100% | 50% |
|---|---|---|
| Ethanol | 100 ± 0a | 80 ± 10a |
| Methanol | 100 ± 0a | 27 ± 2b |
| Acetone | 10 ± 10b | |
| Water | 5 ± 5b | |
| Control | 0 ± 0b | 0 ± 0c |

Mean±Standard Error of the Mean (SEM) of two replicates. Means within a column followed by the same letter are not significantly different at α=0.05 level. (SAS Institute, 1991).

To be considered an "effective" pesticide when tested using a soil assay procedure, one would expect to see results of 100% with a 100% concentration and 100% with a 50% concentration. The results shown in Table 9 indicate that the ethanol extract killed western corn rootworm larvae in soil very effectively at full strength, 80% strength, and at 50% strength. Methanol was effective at 100%, while acetone and water were less effective, respectively. The soil bioassay shows that there are insecticidal materials in the extracts, especially in the ethanol and methanol extracts. The data is of comparative value, but the potency of the extracts is not very promising for any kind of insect control in the soil.

D) Aquatic Assays
1) Yellow Fever Mosquito (Larvae)

Tables 10 and 11 show the toxicities of crambe seed meal extracts and sinigrin and epi-progoitrin breakdown products, respectively, on the yellow fever mosquito after 24 hours.

TABLE 10

Toxicities of crambe meal extracts on the yellow fever mosquito (*A. aegypti*) after 24 h

| Extract | $LC_{50}$ ($\mu mol/ml$) | 95% FL |
|---|---|---|
| Ethanol | 0.64 | 0.38, 0.89 |
| Acetone | 0.76 | 0.45, 1.08 |
| Water | 1.20 | 0.85, 1.56 |

TABLE 11

Toxicity of sinigrin and epi-progoitrin breakdown products to the yellow fever mosquito (*A. aegypti*) (Percent mortality at 24 h)

| Compound | % mortality at 1 ppm |
|---|---|
| AITC | 83% |
| ATC | 57% |
| CHB | 17% |
| AC | 3% |

To be considered an effective aquatic pesticide, a compound would need to show an $LC_{50}$ of less than about 0.01 $\mu mol/ml$ or demonstrate 100% mortality at about 0.01 ppm. The highly toxic aquatic commercial insecticide temephos, for example, shows comparable values, and is considered to be an effective control mosquito. A moderately effective aquatic pesticide would show an $LC_{50}$ of less than about 0.1 $\mu mol/ml$ or demonstrate 100% mortality at about 0.1 ppm and a relatively weak aquatic pesticide would have a $LC_{50}$ of less than about one (1) $\mu mol/ml$ or demonstrate 100% mortality at about one (1) ppm. The results from Table 10 indicate that only the ethanol and acetone extracts are even mildly toxic to the yellow fever mosquito larvae, and would be considered relatively weak pesticides. The results from Table 11 indicate that only AITC and ATC are even mildly toxic to the yellow fever mosquito, but would also be considered relatively weak pesticides. Regarding the crude water extract results in Table 10, this again confirms previous work in the industry which indicate that such extracts do not possess significant toxicity to warrant consideration as a replacement aquatic pesticide. Regarding the breakdown products from the isolated and purified CHB as obtained through the above-described method, although the results in Table 11 indicate that these compounds are relatively weak aquatic pesticides, it is possible that AITC and ATC, as well as CHB and AC may possess significant toxicity to the yellow fever mosquito when delivered through different routes of exposure.

2) Brine Shrimp

Table 12 shows the toxicities of various sinigrin and epi-progoitrin breakdown products to brine shrimp (*Artemia franciscana*) after 24 hours.

TABLE 12

Toxicities of sinigrin and epi-progoitrin breakdown products to brine shrimp (*Artemia franciscana*) at 24 h

| Compound | % Mortality at 1 ppm |
|---|---|
| AITC | 97 |
| ATC | 47 |
| CHB | 13 |
| AC | 7 |

The results show that AITC is a relatively weak aquatic pesticide, while ATC, CHB and AC are very weak aquatic pesticides. It may be that ATC as well as CHB and AC possess significant toxicity to the brine shrimp when delivered through different routes of exposure.

E) Topical Applications

Table 12A shows the results of the topical application of various sinigrin and epi-progoitrin breakdown products to the adult house fly (*Musca domestica*) after 24 hours.

TABLE 12A

Results of topical application of various sinigrin and epi- progoitrin breakdown products to the adult house fly (*Musca domestica*) after 24 h

| | Percentage mortality at 24 h Dose (μg/fly) | | | | | | | |
|---|---|---|---|---|---|---|---|---|
| Compound | 107 | 101 | 100 | 99 | 97 | 10.7 | 10 | 1 |
| CHB | 55 | | | | | | 0 | |
| Goitrin | | | 5 | | | | | 5 |
| AITC | | | | | 45 | | | |
| AC | | | | | | | 15 | |
| AIC | | 35 | | | | | | |
| dichlorvos | | | | | | | | 95 |
| control | | | | | 5 | | | |

A control value of five (5)% for 100 μg/fly indicates that the acetone solvent used was weakly toxic. Dichlorvos was used as the standard. The dichlorvos value of 95% mortality at 1 μg/fly indicates that dichlorvos is a highly toxic pesticide. As Table 1 2A shows, the various breakdown products of sinigrin and epi-progoitrin are relatively weak pesticides by topical application against the house fly.

VI. Conclusions

The results of the above tests indicate that, as a fumigant, ATC rivals and surpasses chloropicrin in toxicity against the adult house fly (*M. domestica*) and the less grain borer (*R. dominica*), respectively. Specifically, allyl thiocyanate (ATC) was found to be effective against the lesser grain borer (*R. dominica*) in fumigation tests ($LC_{50}=0.55$ μg/cm$^3$), and is more toxic to this species than a commercial standard, chloropicrin ($LC_{50}=1.30$ μg/cm$^3$). ATC is also an effective fumigant on the adult house fly ($LC_{50}=0.10$ μg/cm$^3$), although it is not as effective as dichlorvos ($LC_{50}<0.01$ μg/cm$^3$).

In aquatic systems, AITC is the most effective compound among those tested. Allyl isothiocyanate (AITC) demonstrated activity against the brine shrimp (*Artemia franciscana*) (97% mortality at 1 ppm), and the larvae of the yellow fever mosquito (*Aedes aegypti*) (83% mortality at 1 ppm) in toxicity tests.

The seed meal itself was toxic to the larvae of *M. domestica* (80% mortality at 50% of larval medium). Ethanolic extraction of the seed meal appears to be the most efficient of the methods attempted to extract the active components in *C. abyssinica* seed meal. Specifically, unpurified ethanolic extracts of *C. abyssinica* seed meal (with ethanol removed) had activity against the larvae of the western corn rootworm *Diabrotica virgifera* (80% mortality in 24 hr at 1:1 dilution) and the larvae of *A. aegypti* ($LC_{50}=0.64$ μmol/ml).

In topical applications against the house fly, the epi-progoitrin and sinigrin breakdown products tested were relatively weak pesticides. Further testing, however, against other pests may result in higher toxicity. Also further testing of other breakdown products of glucosinolates, or with breakdown products isolated and purified by suitable alternative methods may result in higher toxicity.

These results show that glucosinolates, and specifically their hydrolysis products, can be used as insect control agents. These compounds are fully and rapidly biodegradable and are not persistent in the environment.

EXAMPLE 2

Synthesized CHP (Analog of CHB) as a Pesticide

I. Starting Material—Synthesis of CHP

A) Synthesis of 1-Cyano-1-hydroxy propene (CHP) by "TMS" Method.

The reaction proceeded in two parts:

Part 1: A 250 ml three necked flask was charged with 50 ml dichloromethane, 6.72 g (0.12 mol) acrolein, and 600 mg (1.9 mmol) zinc iodide. The mixture was cooled in an ice bath and 13.9 g (0.14 mol) trimethylsilyl cyanide was added slowly. The ice bath was removed after 3 hr. and the reaction allowed to proceed at room temperature overnight. The reaction was concentrated using rotary evaporation at 20 in Hg vacuum at 25° C. until there was no noticeable reduction in volume.

Part 2: Without purification, the remaining portion was dissolved in 50 ml tetrahydrofuran and 30 ml 3N HCl was added slowly. This was placed on an ice bath and stirred for three hours. The ice bath was removed and the reaction allowed to run for an additional hour. The solution was poured into a 250 ml separatory funnel and 30 ml distilled water was added. The aqueous phase was separated and back-extracted with two (2) 100 ml portions of diethyl ether. The ethereal portions were combined with the tetrahydrofuran portion and passed over anhydrous Na2SO$_4$. The solvent was removed by rotary evaporation at the conditions mentioned above. The resulting product was purified using open column chromatography with 10:4 hexane:ethyl acetate solvent system. The solvent was removed by rotary evaporation at the conditions as described above in Example 1.

B) Synthesis of 1-CyAno-1-hydro propene (CHP) by the "KCN" Method.

A 500 ml two-necked flask was charged with 200 ml anhydrous diethyl ether, 8.8 ml (6.72 g, 0.12 mol) acrolein, and 9.24 g (0.14 mol) potassium cyanide. 8.5 ml glacial acetic acid was added slowly. The reaction ran at room temperature for 24 h. A saturated water solution of NaHCO$_3$ was added to the reaction mixture to dissolve any precipitate and unreacted KCN. The etheral portion was washed three (3) times with the saturated NaHCO$_3$ solution. The ether portion was passed over anhydrous Na$_2$SO$_4$ and concentrated by rotary evaporation at 20 in. Hg vacuum at 25° C. The resulting product was purified using open column chromatography with 10:4 hexane:ethyl acetate solvent system. The solvent was removed by rotary evaporation at the conditions described above in Example 1.

II. Testing Organisms and Assays

CHP and the standards chloropicrin and dichlorvos were tested against the lesser grain borer and the adult house fly in fumigation assays as shown in Example 1.

III. Test Proceducers

A) Fumigation Assay

The fumigation assays with the lesser grain borer and adult house fly were carried out as described above in Example 1.

B) Topical Application

The topical application with the adult house fly was carried out as described above in Example 1.

IV. Results

A) Fumigation Assay

The results of the fumigation assays with CHP and the commercial standard fumigants chloropicrin and dichlorvos are shown in Table 13.

TABLE 13

Fumigation toxicity of CHP with the lesser grain borer and adult house fly after 24 h

| Compound | Lesser grain borer $LC_{50}$ ($\mu g/cm^3$) | adult house fly $LC_{50}$ ($\mu g/cm^3$) |
|---|---|---|
| CHP | 0.37 | 0.15 |
| chloropicrin | 1.3 | 0.08 |
| dichlorvos | 0.29 | 0.011 |

Table 13 shows that CHP is a highly effective fumigant against the lesser grain borer as it is nearly as effective as dichlorvos as a fumigant and three times more effective than chloropicrin. CHP is highly effective as a fumigant against the adult house fly as it was about only 1.9 times less effective than the chloropicrin standard.

B) Topical Application

Table 13A shows the result of the topical application of CHP against the adult house fly (*Musca domestica*) after 24 hours.

TABLE 13A

Results of the topical application of CHP against the adult house fly (*Musca domestica*) after 24 h
Percentage mortality at 24 h
Dose ($\mu g/fly$)

| Compound | 100 | 98 | 9.8 | 1 |
|---|---|---|---|---|
| CHP |  | 100 | 5 |  |
| dichlorvos |  |  |  | 95 |
| Control | 5 |  |  |  |

As Table 13A shows, CHP was a relatively weak pesticide by topical 10 application against the house fly.

V. Conclusions

CHP, which was shown to be highly effective against two test species, can be considered a suitable replacement for fumigants which are being banned, replaced or phased out, as it is generally known that when a pesticide or biopesticide demonstrates high effective for test specimens, such as those included above, it is likely going to be effective against most other pests as a fumigant as well. (See also Table 23 discussed below on page 44). As a biopesticide, CHP can likely be registered on the EPA fast-track. Further, since CHP is a close analog of a naturally occurring breakdown product of epi-progoitrin, i.e., CHB, it is likely to be less toxic in the environment and to vertebrate animals than conventional fumigants. It is likely that CHP will also be moderately to highly effective via other routes of exposure, including aquatic, topical and dietary. CHP was weakly effective against the house fly by topical application. Further testing, however, against other pests may result in higher toxicity. Also, further testing of CHP isolated and purified by suitable alternative methods may result in higher toxicity.

EXAMPLE 3

Other Cyanohydrin Analogs as Pesticides

I. Starting Material

Synthesis of Other Cyanohydrin Analogs

As noted previously, two of the above cyanohydrins are naturally-occurring in plants. Specifically, DMK-CNOH is found in flax and MEK-CNOH is found in flax and cassava. These cyanohydrins, as well as others, including MVK-CNOH, 2-methylbutyraldehyde cyanohydrin, 2-methylvaleraldehyde cyanohydrin, 3-methylbutanone cyanohydrin, 2-methyl-2-butenal cyanohydrin, 2-cyclohexene-1-one cyanohydrin, and 2-nitromandelonitrile cyanohydrin were synthesized by the following two methods:

A) Synthesis of Cyanohydrins by the "TMS" Method.

This method is based on that of Gassman and Talley, *Organic Synthesis* 60: 14. The aldehyde or ketone corresponding to the desired cyanohydrin is dissolved in dichloromethane with a catalytic amount $ZnI_2$. The solution is heated for large, hindered ketones, cooled on an ice bath for small compounds, or left at room temperature for compounds of intermediate size. Trimethylsilyl cyanide is added and the reaction allowed to run until the reactant aldehyde or ketone is no longer detected by thin-layer chromatography. Dichloromethane is removed from the reaction mixture by rotary evaporation and the resulting product, without undergoing any further purification, is mixed with tetrahydrofuran and 3N hydrochloric acid. Upon completion of the reaction (evidenced by the appearance of a new spot on thin-layer chromatography), the reaction mixture is extracted with water three times. The aqueous phase is back-extracted three times with diethyl ether. The ethereal portions are combined with the tetrahydrofuran portion and the solvents are removed by rotary evaporation. The resulting product is them further purified as necessary.

B) Synthesis of Cyanohydrins by the "KCN" Method.

Potassium cyanide (KCN) is added to anhydrous diethyl ether and stirred with a magnetic stirbar. The aldehyde or ketone corresponding to the desired cyanohydrin is slowly added to the reaction mixture. A stoichiometric amount of glacial acetic acid is added and the reaction allowed to proceed until the reactant aldehyde or ketone is no longer detected by thin-layer chromatography. Saturated $NaHCO_3$ water solution is added to the reaction mixture to dissolve remaining KCN and resulting potassium acetate, as well as neutralize any remaining acetic acid. The reaction mixture is washed three times with the saturated $NaHCO_3$ solution. The diethyl ether is removed by rotary evaporation and the product purified as necessary.

II. Test Organisms and Assays

The cyanohydrin analogs, and the standards chloropicrin and dichlorvos were tested against the lesser grain borer and the adult house fly in fumigation assays as shown in Example 1.

III. Test Proceducers

The fumigation assays with the lesser grain borer and adult house fly were carried out as described above in Example 1.

IV. Results

The results of the fumigation assays with the cyanohydrin analogs and the commercial standard fumigants chloropicrin and dichlorvos are shown in Table 14.

TABLE 14

Fumigation toxicity of cyanohydrin analogs with the lesser grain borer and adult house fly after 24 h

| Compound | Lesser grain borer LC$_{50}$ ($\mu$g/cm$^3$) | Adult house fly LC$_{50}$ ($\mu$g/cm$^3$) |
|---|---|---|
| DMK-CNOH | 0.25 | <0.07 |
| MEK-CNOH | 0.27 | 0.09 |
| MVK-CNOH | 0.92 | 0.21 |
| chloropicrin | 1.3 | 0.08 |
| dichlorvos | 0.29 | 0.011 |
| 2-methylbutyraldehyde cyanohydrin | >20 | >20 |
| 2-methylvaleraldehyde cyanohydrin | >20 | >20 |
| 3-methylbutanone cyanohydrin | >20 | >20 |
| 2-methyl-2-butenal cyanohydrin | >20 | >20 |
| 2-cyclohexen-1-one cyanohydrin | >20 | >20 |
| 2-nitromandelonitrile cyanohydrin | >20 | >20 |

Table 14 shows that DMK-CNOH is a highly effective fumigant against the lesser grain borer as it is slightly more effective than dichlorvos as a fumigant and three times more effective than chloropicrin. DMK-CNOH is also a highly effective fumigant against the adult house fly, as it is nearly as effective as dichlorvos and slightly more effective than chloropicrin. MEK-CNOH can also be considered a highly effective fumigant for the same reasons as DMK-CNOH, except that MEK-CNOH is "about as effective" as chloropicrin. Although MVK-CNOH is about three times less effective than dichlorvos it is still considered a moderately effective fumigant as compared with that standard. When compared against chloropicrin, however, MVK-CNOH can be considered a highly effective fumigant, as it is about 1.5 times more effective than chloropicrin against the lesser grain borer. Further, although MVK-CNOH is about 20 times less effective against the house fly than dichlorvos, it is only about 2.5 times less effective against the house fly than chloropicrin, and so can be considered a moderately to highly effective fumigant against the adult house fly. The other six compounds showed virtually no pesticidal activity as fumigants against the lesser grain borer and adult house fly.

Although only these particular analogs were tested, it is likely other analogs in the cyanohydrin class are also excellent pesticides including, but not limited to, those synthesized from diethyl ketone, isobutyraldehyde, propionaldehyde, cyclobutanone, fluoroacetone, and di-tert-butyl ketone.

V. Conclusions

DMK-CNOH and MEK-CNOH, which are highly effective against the above two test specimens, and MVK-CNOH, which is moderately to highly effective, are all suitable replacements for fumigants which are being banned, replaced or phased out. As biopesticides, these analogs can be registered on the EPA fast-track and will likely possess less toxicity in the environment and to vertebrate animals than conventional fumigants. It is likely that these analogs will also be moderately to highly effective via other routes of exposure, including aquatic, topical and dietary.

EXAMPLE 4

Derivatives of CHP as Pesticides

I. Starting Materials—Synthesis of the Derivatives

In this example, several carboxylic acids were esterified with CHP including acetic, propionic, pivalic, 3-chloropropionic, chloroacetic, propiolic, decanoic, citronellate, and cinnamic acids. Two acids (cinnamic acid and decanoic acid) are actually very close relatives of monoterpenoids, but do not technically fulfill the precise definition of a monoterpenoid, and so are included here in Example 4 rather than in Example 5 below. Specifically, cinnamic acid is one carbon atom short of the required 10-carbon skeleton, while decanoic acid has the 10-carbon atoms, but is completely linear, as opposed to the requisite branching pattern of a monoterpenoid.

The esterification reactions were achieved by using dicyclohexylcarbodiimide (DCC) as a condensing agent and 4-(dimethylamino) pyridine (DMAP) as a catalyst. The alcohol CHP (0.01 mol) and the acid of choice (0.01 mol) were dissolved or suspended in 15 ml of dry methylene chloride (CH$_2$Cl$_2$) solvent in a 50-ml round-bottom flask. The solvent can also be dry toluene or chloroform. Equimolar DCC was added, with constant stirring at room temperature, for a few hours or for as long as several days for certain acids. In some reactions, i.e., for some acids, DMAP was also required in the reaction mixture to obtain the desired ester. The reaction was exothermic, and the yields varied from about 75% to about 100%. The ester products were purified using silica gel column chromatography.

The synthesis is shown as follows:

$$\underset{R}{\overset{O}{\underset{\|}{C}}}\text{---OH} + R'\text{---OH} \xrightarrow[\text{2. DMAP (catalyst)}]{\text{1. Dry CH}_2\text{Cl}_2} \underset{R}{\overset{O}{\underset{\|}{C}}}\text{---OR'}$$
3. DCC (equimolar)

where R can be methyl, ethyl, t-butyl, chloroethyl, chloromethyl, ethynyl or nonyl. The chemical structures, names, and abbreviations for the CHP derivatives which were tested are shown in Table 15 below.

TABLE 15

CHP Derivatives Tested

| Structure | Name | Abbreviation |
|---|---|---|
| [CN-CH=CH-CH(-)-O-C(=O)-CH$_3$] | CHP acetate | CHP-Ace |

TABLE 15-continued

CHP Derivatives Tested

| Structure | Name | Abbreviation |
|---|---|---|
| (structure) | CHP propionate | CHP-Pro |
| (structure) | CHP 3-chloropropionate | CHP-ClPro |
| (structure) | CHP pivalate | CHP-Piv |
| (structure) | CHP 4-fluorobenzoate decanoate | CHP-4FB |
| (structure) | CHP decanoate | |
| (structure) | CHP propiolate | |
| (structure) | CHP cinnamate | |
| (structure) | CHP citronellate | |

II. Test Organisms and Assays

A) Fumigation Assays

Due to relatively low yields of less than about 10% from this particular synthesis, 4-fluorobenzoate decanoate, 3-chloropropionic, chloroacetic acid and propiolic acid were not tested in this experiment for use as pesticides. It is possible that synthesis by another method will result in higher yields for these CHP derivatives, and that they will likely show effectiveness as pesticides similar to the effectiveness shown by the CHP derivatives which were tested. Each of the other CBP derivatives and the standards chloropicrin and dichlorvos were tested against the lesser grain borer and the adult house fly in fumigation assays.

B) Topical Application

Various derivatives of CHP and the standard chlorpyrifos were tested against the adult house fly in topical applications, in acetone solution. The control treatment was just the acetone solvent.

C) Whole Body Exposure

Various derivatives of CHP, a solvent control, and a standard (rotenone) and were tested against brine shrimp in whole body exposures to determine their aquatic toxicity.

III. Test Proceducers

A) Fumigation Assays

The fumigation assays with the lesser grain borer and adult house fly were carried out as described above in Example 1.

B) Topical Application

Acute topical toxicities against the adult house fly were carried out according to the method described in Example 1, with CIP derivatives being used in lieu of purified glucosinolate breakdown products.

C) Whole body exposure

The whole body exposure tests against the brine shrimp were performed the same as the aquatic assays described in Example 1.

IV. Results

A) Fumigation Assays

The results of the fumigation assays with the CHP derivatives and commercial standard fumigants chloropicrin and dichlorvos against the lesser grain borer and adult house fly are shown in Table 16.

TABLE 16

Fumigation toxicity of CHP derivatives with the lesser grain borer and adult house fly after 24 h

| Compound | Lesser grain borer $LC_{50}$ ($\mu g/cm^3$) | Adult house fly $LC_{50}$ ($\mu g/cm^3$) |
|---|---|---|
| CHP-Ace | 0.37 | 0.26 |
| CHP-Pro | 0.70 | 0.66 |
| CHP-Piv | 2.4 | 1.37 |
| chloropicrin | 1.3 | 0.08 |
| dichlorvos | 0.29 | 0.011 |

Table 16 shows that CHP-Ace is a highly effective fumigant against the lesser grain borer as it is only slightly less effective than dichlorvos and three times more effective than chloropicrin. CHP-Ace is a moderately effective fumigant against the adult house fly as it is about 20 times less effective than dichlorvos and chloropicrin. CHP-Pro is a highly effective fumigant against the lesser grain borer as compared with dichlorvos as it is only about 2.5 times less effective, and is about 1.5 times more effective than chloropicrin. CHP-Pro is a relatively weak to moderately effective fumigant against the adult house fly as it is about 60 times less effective than dichlorvos and chloropicrin. CHP-Piv is a moderately effective fumigant against the adult house fly as it is about ten (10) times less effective than dichlorvos, but only about two (2) times less effective than chloropicrin. CHP-Piv is a relatively weak fumigant against the house fly as it is about 100 times less effective than chloropicrin and dichlorvos, a highly effective fumigant against the adult house fly.

Although only these particular derivatives were tested, it is likely other types of CHP derivatives may also be very good fumigants, including, but not limited to CHP chloroacetate, CHP acrylate, and CHP ethers such as CHP ethyl ether, CHP isopropyl ether, CHP fluoroalkyl ethers, CBP propargyl ether, and CHP ethynyl ether.

B) Topical Application

The results of the topical application against the adult house fly with various CHP derivatives are shown in Table 17.

TABLE 17

Toxicity of CHP derivatives to the adult house fly (*Musca domestica*) by topical application

| Compound | Percentage mortality at 24 h Dose ($\mu g/fly$) | | | | | | | |
|---|---|---|---|---|---|---|---|---|
| | 102 | 100 | 99 | 97 | 10 | 9.9 | 9.7 | 1 |
| CHP decanoate | | 100 | | | 64 | | | 0 |
| CHP cinnamate | | 87 | | | 50 | | | 0 |
| cinnamic acid | | 0 | | | 0 | | | 0 |
| citronellic acid | | 100 | | | 91 | | | 0 |
| CHP acetate | 100 | | | | | | 0 | |
| CHP propionate | | | 100 | | | | 0 | |
| CHP pivalate | | | | 80 | | | 0 | |
| chlorpyrifos | | | | $LD_{50} = 0.08$ $\mu g/fly$ | | | | |
| control | | | | | | | 0 | |

As Table 17 shows, the CHP derivatives are relatively weak as topical pesticides as they are only slightly toxic to the house fly. A control value of zero (0) for 100$\mu g$/fly indicates that the acetone solvent used was nontoxic. Chlorpyrifos, an organophosphate conventional insecticide was used as the standard. The chlorpyrifos $LD_{50}$ value of 0.08 $\mu g$/fly indicates that a dose of 0.08 $\mu g$/fly would produce 50% mortality in 24 hours. (A standard effective insecticide by topical application is expected to have about 100% mortality per 100 $\mu g$ dose). Accordingly, these CBP derivatives are very weak biopesticides as compared with the chlorpyrifos standard, since for example, ten (10) $\mu g$/fly of CHP decanoate and CHP cinnamate only kill around 50% in 24 hours, as compared to 0.08 $\mu g$/fly of chlorpyrifos that kills 50%. In other words, these biopesticides are about 125 times less toxic than chlorpyrifos. As shown above, cinnamic acid, is also not an effective biopesticide to the house fly by topical application.

Although the esters tested are weakly insecticidal by topical application against the adult house fly, it is possible with improvements to either an ester derivative of CHP or an ether derivative of CHP, that the CHP organic group can be delivered more effectively by contact i.e., topical toxicity. Further, it is possible that these and other CHP derivatives may be more toxic against other pests by topical application.

C) Whole Body Exposure

The results of the whole body exposure to brine shrimp with various CHP derivatives and a control and a standard (rotenone) is shown in Table 18.

TABLE 18

Toxicity of CHP derivatives to the brine shrimp (*Artemia francisana*) by topical application

| | concentration (ppm) | | |
|---|---|---|---|
| Compound | 100 | 10 | 1 |
| CHP decanoate | 100 | 95 | 15 |
| CHP cinnamate | 100 | 100 | 95 |
| cinnamic acid | 100 | 45 | 30 |
| citronellic acid | 100 | 65 | 40 |
| rotenone | | | 100 |
| control | 0 | | |

Note:
Mortality is the average % of two replicates. Each replicate contains 10–15 individual insects or shrimp.

he above results indicate that the two CHP derivatives are more toxic than the two acids. CHP cinnamate is moderately toxic, while the other three are relatively weak biopesticides. Rotenone was used as the standard biopesticide, while the control treatment constituted exposure only to the solvent acetone, in which the biospesticides were dissolved.

V. Conclusions

The ester derivatives of CHP (or other cyanohydrins like DMK-CNOH, MEK-CNOH) are more stable than CHP, which is considered to be the toxophore in the above esters. These compounds, therefore, are somewhat protected from degradation by physical, chemical, and biological agents. This protection may be valuable in prolonging their shelf-life.

A) Fumigation Assays

CHP-Ace and CHP-Pro is highly effective against the lesser grain borer, and CHP-Piv is moderately effective against the lesser grain borer. CHP-Ace is also moderately effective against the adult house fly. All of these compounds are suitable replacements for fumigants which are being banned, replaced or phased out. As biopesticides, these derivatives can likely be registered on the EPA fast-track and will likely possess less toxicity in the environment and to vertebrate animals than conventional fumigants. Although CHP-Piv demonstrated relatively weak efficacy as fumigants against the adult house fly, since this compounds is derived from a natural source, it may still offer a viable alternative as a fumigant in certain applications as compared with the more toxic conventional fumigants.

B) Topical Application

Although the esters in Table 17 do not have as high a mortality by topical application against the adult house fly as compared with the esters delivered by fumigation in Table 16, these biopesticides demonstrate a sufficiently high mortality to be considered a viable replacement for conventional topical pesticides. These esters, as well as other derivatives of CHP may be moderately to highly effective biopesticides via aquatic or dietary routes of exposure. It should be noted, however, that these pesticides are less volatile due to their higher molecular weight, but can still deliver toxicity within the insects, although with a slower reaction time.

C) Whole Body Exposure

The aquatic toxicity tests which result in a whole-body exposure for the two arthropods tested, show that the CHP derivatives have potential for insect control in aquatic applications.

EXAMPLE 5

Monoterpenoid and Cyanohydrin Hybrid Biopesticides

I. Background

By combining synthetic alcohols with natural monoterpenoids in esters, novel hybrids were created with enhanced activity from the parent monoterpenoids. In this example, several ester derivatives of citronellic acid, trans-cinnamic acid and geranoic acid were synthesized in a series of derivatizations to esters with 3-cyano-3-hydroxy-1-propene (CHP). Esters that were made from CHP (alcohol) and a monoterpenoid acid represent a hybrid or combination of two types of biopesticides: CHP and monoterpenes. Cyanohydrins made from monoterpenoid and related aldehydes also represent hybrids of the CHP/cyanohydrin class and the monoterpenoid class.

II. Starting Material

A) Synthesis of Cyanohydrin/Monoterpenoid Hybrids

Cyanohydrins made from monoterpenoids were synthesized from the monoterpenoid aldehyde, using the method listed in Example 3. The chemical structures, names, and abbreviations for the cyanohydrin/monoterpenoid hybrids which were tested are shown in Table 19 below:

TABLE 19

| Cyanohydrin/monoterpenoid hybrids tested |
| --- |
| [structure] CHP geranoate |
| [structure] citronellyl cyanohydrin |
| [structure] citryl cyanohydrin |
| [structure] cinnamyl cyanohydrin |

III. Testing Organisms and Assays

A) Topical Applications

Each of the hybrids (except for CHI) geraniate), the acetone control, and the standard chiorpyrifos were tested against the adult house fly in topical applications. CHP geraniate was not tested due to a relatively low yield from this particular synthesis. It is possible that synthesis by another method will result in higher yields for CHP geraniate, and that it will likely show effectiveness as a pesticide similar to the effectiveness shown by the CHP hybrids which were tested.

B) Whole Body Exposure

Each of the hybrids, the control, and rotenone as a standard were tested against the brine shrimp in whole body exposures.

IV. Test Procedures

A) Fumigation Assays

The fumigation assays with the lesser grain borer and brine shrimp were carried out as described above in Example 1.

B) Topical Applications

The topical applications with the adult house fly were carried out as described above in Example 4.

C) Whole Body Exposure

The whole body exposure tests against the brine shrimp were performed the same as the aquatic assays described in Example 1.

V. Results

A) Topical Applications

The mortality of the adult house fly against citronellyl cyanohydrin, citryl cyanohydrin, and cinnamyl cyanohydrin is shown below in Table 20.

TABLE 20

Mortality of adult house fly (*Musca domestica*) by topical application

| | Percentage mortality at 24 h Dose ($\mu$g/fly) | | |
| --- | --- | --- | --- |
| Compound | 50 | 6 | 1 |
| citronellyl cyanohydrin | 10 | 14 | |
| citryl cyanohydrin | | 9 | 8 |
| cinnamyl cyanohydrin | 100 | 9 | |
| chlorpyrifos | $LD_{50}$ = 0.08 $\mu$g/fly | | |
| control | 0 | | |

As Table 20 shows, cinnamyl cyanohydrin is a relatively weak pesticide against the house fly as it is only slightly toxic to this pest as compared to chlorpyrifos. Citronellyl cyanohydrin and citryl cyanohydrin are considered "not active" as pesticides against the house fly.

B) Whole Body Exposure

The mortality of brine shrimp against citryl cyanohydrin and cinnamyl cyanohydrin is shown in Table 21.

TABLE 21

Mortality of brine shrimp (*Artemia franciscana*) by whole hody exposure

| | concentration (ppm) | | |
| --- | --- | --- | --- |
| Compound | 100 | 10 | 1 |
| citryl cyanohydrin | 87 | 0 | 0 |
| cinnamyl cyanohydrin | 100 | 15 | 25 |
| rotenone | — | — | 100 |
| control | 0 | | |

Note:
Mortality is the average % of two replicates. Each replicate contains 10–15 individual insects or shrimp.

As Table 21 shows, both hybrids are weakly (slightly) to moderately toxic in the aquatic bioassay.

VI. Conclusions

For both the topical application and the whole body (aquatic) applications, the hybrids tested are weakly to moderately toxic to the target organisms, i.e., the house fly and brine shrimp, respectively. This indicates that these hybrids may likely be effective against different species via different delivery modes, or under circumstances where only environmentally-friendly biopesticides can be used.

EXAMPLE 6

CHB, CHP, CHP-Derivatives and Analogs as Nematicides (Against the Soybean Cyst Nematode)

I. Starting Material

Biopesticides prepared as described in Examples 1, 2, 3, and 4, were tested against the soybean cyst nematode (SCN) (*Heterodera glycines*) for nematicidal activity.

II. Testing Organisms and Assays

CHB, CBp, CHP-Ace, CHP-Piv and MEK-CNOH were tested against soybean cyst nematode eggs.

III. Test Procedures

Hatching of the eggs was inhibited over a 28-day assay by zero (0) to 99% at ten (10) or 100 ppm ($\mu$g/ml) of the compound in water. Specifically, SCN eggs were extracted from SCN females and were surface disinfected. Approximately 6,000 eggs were then placed on a small plastic sieve (about 0.8 inches in diameter). The eggs were then bathed in a test solution in a small plastic tray in complete darkness at 25° C. Every other day, for 28 days, larval SCN (newly hatched) were counted in the tray for a total percentage of eggs that hatched. Water served as the control. Data was tallied after 14 and 28 days.

The SCN egg hatch is tested in water because the eggs are present in the soil-water layer (a thin film of water on the soil particles) in the soil.

IV. Results

Table 22 shows the nematicidal activity of various biopesticides of the present invention.

TABLE 22

Nematicidal activity of natural insecticides derived from crambe and insect fumigants related to natural products - effect of compounds on hatch of soybean cyst nematode eggs

| COMPOUND TESTED | CONC. (ppm) | DIFFERENCE IN HATCH* |
|---|---|---|
| CHB | 10 | −70% |
|  | 100 | −73% |
| CHP | 10 | −69% |
|  | 100 | −99% |
| CHP-ACE | 10 | −58% |
|  | 100 | −99% |
| CHP-PIV | 10 | −25% |
|  | 100 | −83% |
| MEK-CNOH | 10 | +2% |
|  | 100 | −83% |

*Difference compared to water (untreated) after 14 days

These results demonstrate that CHB, CHP, two esters of CHP, and one analog of CHP are highly toxic to the eggs of the soybean cysts nematode (SCN). Aldicarb is the only product labeled for SCN control, but is currently not being used. This is in part because the economics are unfavorable, but also because it is extremely toxic, as it is the most toxic insecticide registered, having a mammalian $LD_{50}$ equal to one (1) mg/kg.

V. Conclusions

It is likely that these compounds will also kill juvenile SCN. This is assumed to be true, because it is known that commercial fumigants, such as aldicarb and methyl bromide, which are highly toxic against insects, also kill nematodes, including eggs and juveniles.

EXAMPLE 7

CHR, CHP, CHP-Derivatives and Analogs as Nematicides (Against the Root-Knot Nematode)

I. Starting Material

CHP, CHP-Ace, and MEK-CNOH were prepared as described in Examples 1, 2, 3 and 4. Both mandelonitrile and benzyl isothiocyanate were purchased from Aldrich Chemical Co. in Milwaukee, Wis. The purity of these purchased compounds was at least about 98%.

II. Testing Organisms and Assays

The above compounds were tested against root-knot nematode (RKN) (*Meloidogyne incognita*) eggs for nematicidal activity.

III. Test Procedures

Hatching of RKN eggs was inhibited over a 28-day assay using 100 ppm ($\mu$g/ml) of a compound in water. Specifically, RKN eggs were extracted from RKN females and were surface disinfected. Approximately 6,000 eggs were then placed on a small plastic sieve (about 0.8 inches in diameter). The eggs were then bathed in a test solution in a small plastic tray in complete darkness at about 25° C. Every other day, for 28 days, larval RKN (newly hatched) were counted in the tray for a total percentage of eggs that hatched. The RKN egg hatch is tested in water because the eggs are present in the soil-water layer (a thin film of water on the soil particles) in the soil.

The two routes of exposure used were contact and fumigation, as described in Example 6 for the soybean cyst nematode. Distilled water ($dH_2O$) served as the control. Approximately 0.5 ml of each compound was applied to the eggs. Data was taken on the first day, and every two days thereafter over a period of 22 days.

IV. Results

A. Contact Assays

The results of the contact assays with various compounds and controls against the root-knot nematode egg are shown in Table 23.

TABLE 23

Percent hatch of root-knot nematode eggs following exposure by contact to various biopesticides

| *COMPOUND TESTED | 0 | 2 | 4 | 6 | 8 | 10 | 12 | 14 | 16 | 18 | 20 | 22 |
|---|---|---|---|---|---|---|---|---|---|---|---|---|
| Benzyl isothiocyanate | 0.0 | 5.5 | 19.1 | 30.8 | 39.5 | 48.1 | 53.2 | 60.0 | 62.5 | 63.1 | 63.3 | 63.7 |

TABLE 23-continued

Percent hatch of root-knot nematode eggs following exposure by contact to various biopesticides

| *COMPOUND TESTED | 0 | 2 | 4 | 6 | 8 | 10 | 12 | 14 | 16 | 18 | 20 | 22 |
|---|---|---|---|---|---|---|---|---|---|---|---|---|
| Mandelo-nitrile | 0.0 | 6.1 | 18.8 | 36.3 | 44.3 | 51.6 | 57.3 | 67.1 | 70.2 | 71.3 | 71.8 | 72.2 |
| MEK CNOH | 0.0 | 6.6 | 17.5 | 33.8 | 42.0 | 48.2 | 53.3 | 62.3 | 65.7 | 66.7 | 67.5 | 68.0 |
| CHP | 0.0 | 4.3 | 8.4 | 18.7 | 23.1 | 25.1 | 27.2 | 3.9 | 32.8 | 33.3 | 34.0 | 34.4 |
| CHP-ACE | 0.0 | 0.8 | 1.5 | 4.9 | 5.2 | 5.2 | 5.3 | 5.4 | 5.4 | 5.4 | 5.6 | 5.6 |
| dH$_2$O | 0.0 | 7.6 | 21.9 | 35.0 | 45.8 | 56.8 | 64.5 | 70.2 | 71.4 | 71.9 | 72.0 | 72.2 |

*100 ppm

These results are also shown in FIG. 1 as percent hatch versus time (in days). As Table 23 and FIG. 1 clearly show, the various compositions tested against the root-knot nematode eggs performed quite well as compared with water (dH$_2$O), which resulted in a hatch rate of about 70 percent, which is considered to be a typical hatch rate that occurs naturally. In particular, 0.5 ml of 100 ppm CHP-Acetate displayed "very good" effectiveness. Specifically, percent hatch rates did not exceed 5.6% in any day throughout the 22-day observation period. ("Very good" effectiveness is defined herein to be a hatch rate of between about five (5) and 20 percent). The tested amount of CHP displayed "good" effectiveness, with percent hatch not exceeding 34.4% during the experiment. ("Good" effectiveness is defined herein to be a hatch rate of more than about 20 to about 50%). Other compositions, including the tested amounts of MEK CNOH, mandelonitrile and benzyl isothiocyanate demonstrated "fair" effectiveness (a hatch rate of more than 50% to about 65%).

B. Fumigation Assays

The results of the contact assays with various compounds and controls against the root-knot nematode egg are shown in Table 24.

in the fumigation study. This is likely because CHP-Acetate is not as volatile as CHP.

V. Conclusions

It is likely that these compounds will also kill juvenile RKN. This is assumed to be true, because it is known that commercial nematicides, including both contact insecticides (e.g., aldicarb and oxamyl) and fumigants (e.g., methyl bromide and chloropicrin), which are all highly toxic against insects, also kill nematodes, including eggs and juveniles. It appears that the preferred route of exposure is contact, although a bait or vapor exposure can also be used.

Although only these derivatives were tested, it is likely that other derivatives and analogs described herein, as well as other concentrations, including weaker oncentrations of the compounds tested, may also be very good ftunigants.

EXAMPLE 8

Biological Activity in Soil After Application of CHP-Acetate and Comparison with Methyl Bromide I. Background Various concentrations CHP-Acetate (CHP-Ace) were tested as soil sterilants, fungicides and herbicides in this

TABLE 24

Percent hatch of root-knot nematode eggs following exposure by fumigation to varions biopesticides

| *COMPOUND TESTED | 0 | 2 | 4 | 6 | 8 | 10 | 12 | 14 | 16 | 18 | 20 | 22 |
|---|---|---|---|---|---|---|---|---|---|---|---|---|
| Benzyl iso-thiocyanate | 0.0 | 8.0 | 18.2 | 27.8 | 37.3 | 44.4 | 50.6 | 56.5 | 58.5 | 59.1 | 59.1 | 59.2 |
| mandelo-nitrile | 0.0 | 2.1 | 4.0 | 11.7 | 13.6 | 14.6 | 16.5 | 24.7 | 26.8 | 27.6 | 28.6 | 29.7 |
| MEK CNOH | 0.0 | 3.9 | 14.0 | 24.8 | 28.1 | 31.7 | 38.9 | 50.9 | 55.9 | 58.5 | 60.8 | 63.1 |
| CHP | 0.0 | 1.9 | 3.0 | 13.7 | 13.9 | 14.1 | 14.3 | 16.8 | 17.1 | 17.1 | 18.1 | 19.0 |
| CHP-ACE | 0.0 | 6.8 | 18.1 | 31.4 | 36.5 | 39.8 | 40.8 | 42.1 | 42.4 | 42.6 | 42.6 | 42.6 |
| dH$_2$O | 0.0 | 8.0 | 19.3 | 31.8 | 40.6 | 51.2 | 59.0 | 64.1 | 65.6 | 66.0 | 66.0 | 66.6 |

*100 ppm

Figure 2:
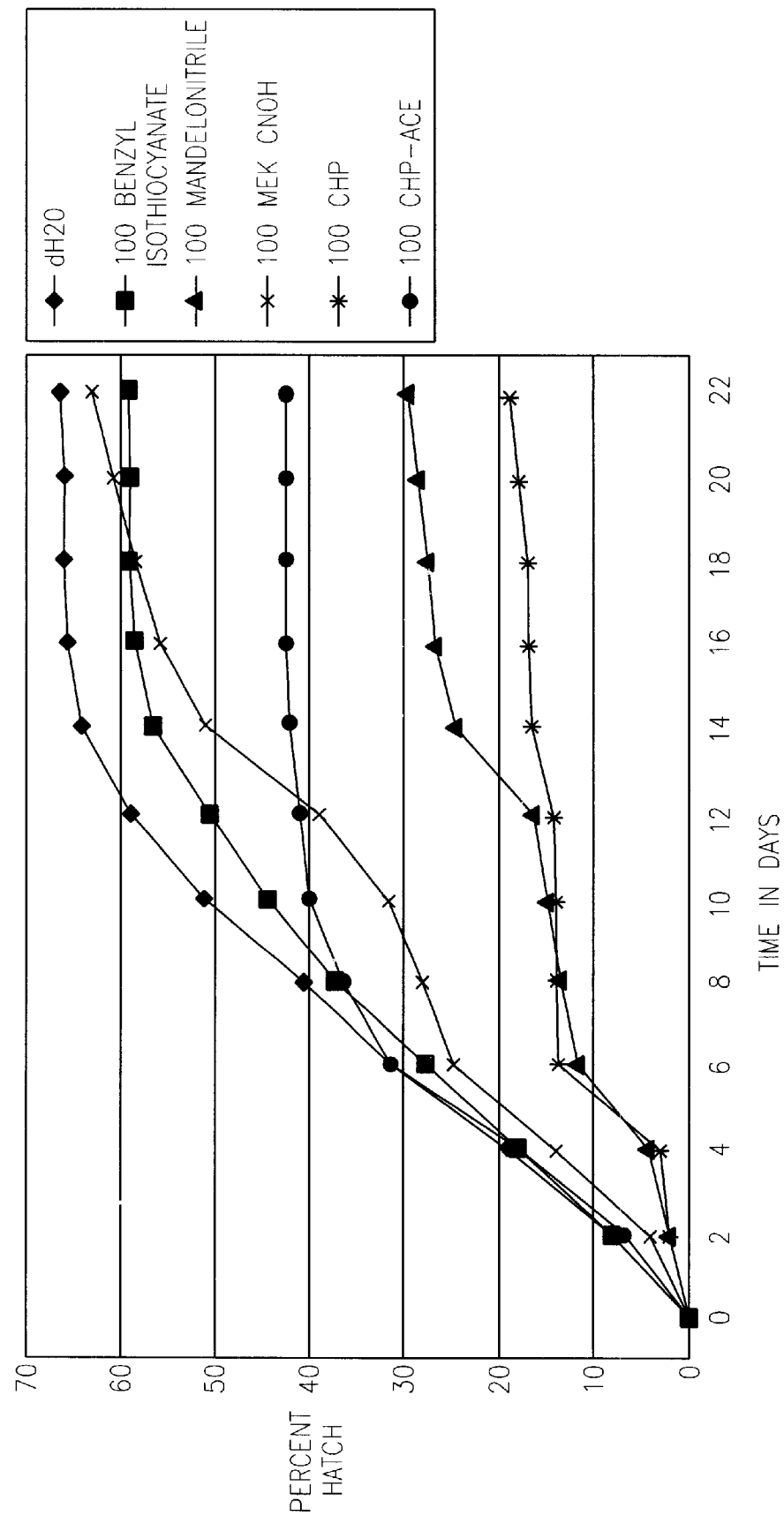
FIG. 2 is a plot of percent hatch versus time for various compounds against root-knot nematode eggs with a volatile route of exposure.

These results are also shown in FIG. 2 as percent hatch versus time in days. As Table 24 and FIG. 2 show, 0.5 ml of 100 ppm CUP displayed "very good" effectiveness. Specifically, the percent hatch of CHP did not exceed 19% over the 22-day period. The tested amount of mandelonitrile showed "good" effectiveness a percent hatch rate not exceeding 29.7% during the length of the experiment. Although, 0.5 ml of 100 ppm. CHP-Ace performed better than the remaining compounds, including the control, with the percent hatch rate not exceeding 42.6% during the experiment, it did not perform as well in this study as it did study. Specifically, bacteria and fungi level, as well as inhibition of weed seed germination were measured in treated and untreated soils. As a comparison, methyl bromide fumigation was performed on the soil, and the effect on microbial respiration was determined. As an additional comparison, the effect of chloropicrin and Telone® on weeds was also determined.

II. Starting Material

CHP-Acetate and methyl bromide in varying concentrations were originally tested in this study. The CHP-Acetate and methyl bromide solutions were made in acetone: 10 ppm CHP-Acetate, 100 ppm CHP-Acetate, 1000 ppm CHP-Acetate, 10,000 ppm CHP-Acetate, 350 ppm MeBr and 2733 ppm MeBr. These particular concentrations of methyl bromide represent field fumigation and structural (facility) fumigation rates, respectively. One-half (0.5) ml was used for each treatment. CHP-Acetate was synthesized as described in Example 4. Methyl bromide was obtained from Great Lakes Chemical Company in West Lafayette, Ind. Two different controls were also used: A blank control (no treatment) and 0.5 ml of acetone solvent control.

Two additional commercial compounds were also tested, namely chloropicrin and Telone®. Chloropicrin was obtained from Aldrich Chemical Company. Telone® was obtained from TCI America in Portland, Oreg. Solutions of these compounds were also made in acetone: 1000 ppm and 10,000 ppm of each. One (1) ml was used for each treatment. A separate control comprising one (1) ml of acetone was also used.

III Test Soil Containing Weed Seeds, Bacteria and Fungi

Fresh soil was collected from the Extension and Research Field of the Department of Entomology, Iowa State University, Ames, Iowa. Generally, the soils were agricultural soils, i.e., a sandy clay-loam, assumed to contain a natural population of soil fungi, soil bacteria and weed seeds, such as foxtail, Lambsquarter, pigweed, and so forth.

IV. Test Procedures

A. Bacteria and Fungi Study

The soils were incubated in a Percival environmental growth chamber made by the Percival Co. in Boone, Iowa. The photo period was 12:12 L:D and temperature was 24° C.±1 inside the chamber. The soils were incubated on a lab bench for 12 hr before six treatments were applied. The six treatments were: blank control, solvent control (0.5 ml acetone), 10 ppm of CHP-Acetate (0.5 ml), 100 ppm of CHP-Acetate (0.5 ml), 1000 ppm of CHP-Acetate (0.5 ml) and 10,000 ppm of CHP-Acetate (0.5 ml). Each treatment had three replications. Ten grams of dry-weight soil was put into a sterilized French square bottle and the six treatments were applied. After the treatment, the soil was placed in the incubator for an additional 46 hr. Ninety (90) ml of sterilized phosphate buffer was then added to each bottle and the bottles were shaken for approximately 30 minutes. Serial dilutions were then carried out, i.e., the solution was progressively diluted by factors of 10. Three or four replicates were used for each concentrate of each compound. Telone® and chloropicrin were used as the commercial standard for comparison. Telone® is known to have fumigation activity against insects, fungi, bacteria and weeds, similar to the efficacy of methyl bromide.

A microdrop plate-count technique was then used to count the number of bacteria and fungi. Generally, this method involves applying the solutions to an agar medium in petri dishes. The number of colony forming units can then be calculated per gram of soil. This method, described in Cooper, J. E., 1979, "Rapid Method for Counting Antibiotic-Resistant Rhizobia in Soils, *Soil Biology* and *Biochemistry*, 11: 433–435, hereby incorporated by reference, provides a means for determining microbial activity in soil. Such results provide a general response of soil microbes to tested compounds in a dose-response assay.

B. Weed Study

In the case of the weed study, three treatments were used initially: A solvent control (0.5 ml acetone), 1000 ppm of CHP-Acetate (0.5 ml), and 10,000 of ppm CHP-Acetate (0.5 ml). Later tests also included one (1) ml treatments of 1000 ppm and 10,000 ppm of chloropicrin and Telone® as noted above. In all cases, 50 g of soil were used in each replication. The soil was put in mason jars, and the mason jars were kept in the greenhouse for three days before the chemical treatments were applied to the surface of the soils. Three replications were done in all instances. For the CHP-Acetate and 0.5 ml solvent control tests, a count of germinated weeds was made at three (3) and 24 days after treatment.

For the chloropicrin and Telone® tests, the mason jars were kept in the greenhouse for four (4) days before the chemical treatments were applied to the surface of the soils. Counts were made ten (10) days after treatment.

C. Microbial Respiration Study

In the case of the microbial respiration study, twenty grams of soil (by dry weight) was placed in stoppered, 250 ml glass jars, and soil moisture was adjusted to −33kPa. The methyl bromide was applied at concentrations of 350 µg/g (i.e., 350 ppm) and 2,733 ppm as noted above. The soils were incubated in the dark at 25° C. The method used to monitor microbial activity in the soil was the measurement of $CO_2$ generated per time interval. Specifically, carbon dioxide efflux was measured at 24-hour intervals after the initial 48-hr. Fumigation period. The sample headspace was purged with moist, $CO_2$-free air and was analyzed using an infrared gas analyzer. Microbial respiration in the fumigated and untreated samples was compared. For a complete description of the test set-up and results, see, "The Influence of Soil Environmental Variables on the Degradation and Volatility of Methyl Bromide in Soil," Rice, J. P. et al., Environmental Toxicology and Chemistry, Vol. 15, No. 19., pp. 1723–1729, 1996, which is hereby incorporated by reference in its entirety.

"Microbial activity" refers to normal respiration, metabolism and growth of soil microorganisms. In this case, microbial activity is referring to "aerobic" activity, i.e., use of oxygen and carbon sources for energy and growth, producing carbon dioxide and water as waste products. "Normal" microbial activity is determined in any given experiment by the activity in the control treatment. "Slightly depressed" activity refers to activity that is about 50% or more of control activity, such that carbon dioxide production is about 50% or more of the production in the control. "Severely depressed" microbial activity refers to activity that is less than 20 percent of control activity, such that carbon dioxide production is less than 20 percent of the production in the control.

V. Results

A. Bacteria and Fungi Study

TABLE 25

Total bacterial count in soil after two days following application of CHP-Acetate

| Treatment (CHP-Acetate 0.5 ml) | Average | Std Deviation (Cells/g dry wt.) |
| --- | --- | --- |
| Blank Control | $4.7 \times 10^6$ | $1.8 \times 10^6$ |
| Solvent Control | $3.2 \times 10^6$ | $0.2 \times 10^6$ |
| 10 ppm | $4.6 \times 10^6$ | $2.6 \times 10^6$ |
| 100 ppm | $16.2 \times 10^6$ | $3.2 \times 10^6$ |
| 1000 ppm | $0.2 \times 10^6$ | $0.02 \times 10^6$ |
| 10,000 ppm | 0.00 | 0.00 |

TABLE 26

Total fungi count in soil after two days following application of CHP-Acetate

| Treatment (CHP-Acetate 0.5 ml) | Average (Cells/ g dry wt.) | Std. Deviation |
|---|---|---|
| Blank Control | $1.9 \times 10^4$ | $0.4 \times 10^4$ |
| Solvent Control | $1.4 \times 10^4$ | $0.4 \times 10^4$ |
| 10 ppm | $2.0 \times 10^4$ | $0.5 \times 10^4$ |
| 100 ppm | $0.5 \times 10^4$ | $0.4 \times 10^4$ |
| 1000 ppm | 0.00 | 0.00 |
| 10,000 ppm | 0.00 | 0.00 |

The results from Table 25 and 26 show that CHP-Acetate, particularly at levels of 1000 ppm and 10,000 ppm can reduce the total bacterial and fungi count significantly, i.e., severely depress microbial growth in both fungus and bacteria after two days. As shown in Table 25, the bacterial count actually increased at a dosage of 100 ppm, indicating that the composition was sufficient to "feed" the bacteria, i.e., provide them with a carbon source, but was not present in an amount sufficient to be inhibitory to the bacteria.

B. Weed Study

Tables 27 and 28 show the average number of germinated weeds following treatment with 0.5 ml of a solvent control and two different concentrations of CHP-Acetate for three different replications after three (3) and 24 days, respectively.

TABLE 27

Number of germinated weed seeds following application of CHP-Acetate (3 days)

| Treatment | Number of Germinated Weeds (Average) | | |
|---|---|---|---|
| Replication | 1 | 2 | 3 |
| Solvent Control | 6 | 8 | 11 |
| 1000 ppm | 0 | 0 | 0 |
| 10,000 ppm | 0 | 0 | 0 |

TABLE 28

Number of germinated weed seeds following application of CHP-Acetate (24 days)

| Treatment | Number of Germinated Weeds (Average) | | |
|---|---|---|---|
| Replication | 1 | 2 | 3 |
| Solvent Control | 10 | 20 | 27 |
| 1000 ppm | 0 | 1 | 0 |
| 10,000 ppm | 0 | 0 | 0 |

Tables 27 and 28 show that CHP-Acetate is effective in inhibiting the germination of weed seeds in soil. It was also observed during testing that CHP-Acetate in both 1000 ppm and 10,000-ppm concentrations can also can kill post-emergent weeds.

Tables 29 and 30 show the average number of germinated weeds following treatment with one (1) ml of a solvent control and two different concentrations of chloropicrin and Telone®, respectively, for three different replications after ten (10) days, respectively.

TABLE 29

Number of germinated weed seeds following application of chloropicrin (10 days)

| Treatment | Number of Germinated Weeds (Average) | | |
|---|---|---|---|
| Replication | 1 | 2 | 3 |
| Solvent Control | 0 | 12 | 3 |
| 1000 ppm | 0 | 3 | 0 |
| 10,000 ppm | 0 | 0 | 0 |

TABLE 30

Number of germinated weed seeds following application of Telone ™ (10 days)

| Treatment | Number of Germinated Weeds (Average) | | |
|---|---|---|---|
| Replication | 1 | 2 | 3 |
| Solvent Control | 0 | 12 | 3 |
| 1000 ppm | 4 | 4 | 8 |
| 10,000 ppm | 0 | 2 | 0 |

Tables 29 and 30 show that both chloropicrin and Telone® are effective in inhibiting the germination of weed seeds in soil. It was also observed during testing that Telone® and/or chloropicrin, in both 1000 ppm and 10,000-ppm concentrations can also can kill post-emergent weeds.

The compositions of the present invention showed effectiveness comparable to chloropicrin and superior to Telone®.

C. Microbial Respiration Study

Table 31 shows the effectiveness of the above treatments as compared to methyl bromide.

TABLE 31

Severity and number of days microbial activity was depressed

| Treatment | Severity | Days |
|---|---|---|
| Control | Normal Activity | 0 |
| 350 ppm MeBr | Slightly Depressed | 4 |
| 2,733 ppm MeBr | Severely Depressed | 24 |
| 10,000 ppm CHP-Acetate | No bacteria or fungal colonies formed after 2 days | |

As Table 31 shows, soil microbial activity was "slightly depressed" after treatment with 350 ppm of methyl bromide, i.e., there was a temporary depression in $CO_2$ efflux, but returned to normal by Day 4. The soil treated with 2733 ppm of methyl bromide exhibited "severe depression" of soil microbial activity for the duration of the 24-day experiment. By comparison, CHP-Acetate at 10,000 ppm completely inhibited growth for two days.

V. Conclusions

While methods and measurement in these studies were slightly different from test to test, application or treatment rates were comparable. The above results show that CHP-Acetate is an effective herbicide, sterilant and fungicide. The results in Tables 25–30 further show that the CHP-Acetate is effective in roughly the same concentrations as methyl bromide.

EXAMPLE 9

Additional Methods for Testing Pesticides

I. Determining Antimicrobial Activity in Soil

Enzyme Assay

The enzyme assay is described in K. Alef and D. Kleiner, "Rapid and Sensitive determination of Microbial Activity in Soils and in Soil Aggregates by Dimethylsulfoxide Reduction," *Biology and Fertility of Soils* 8:349–355 (1989), which is hereby incorporated by reference. Essentially, this method is considered to be a very sensitive technique for quantifying microbial activity, and therefore populations, in soil, by measuring the dimethyl sulfoxide (DMSO)-reductase activity in small flasks of soil. A ten percent solution of DMSO is added to a collected sample of soil. The flask will then be sealed and incubated for three hours at 37 C. The headspace in the flask will then be sampled by gas chromatography for the amount of DMSO formed per hour, per gram of soil, using an FID detector. Again, different concentrations of the compounds of the present invention will be tested for a dose-dependent response. Three or four replicates of this assay will be used for each concentration of each compound and Telone® will be used as the standard.

II. Determining Inhibition of Seed Germination or Toxicity to Germinating Weeds

A. Petri Dish Method

A known number of weed seeds will be distributed in moist oil in petri dishes. The soil will be treated with different concentrations of various compounds of the present invention. Germination will be monitored periodically over the length of the experiment. In one test, germination will be monitored daily over a period of seven days. Two common species of weeds will be utilized, such as foxtail, Lambs quarter, pigweed, and so forth. Three or four replications will be used. Teloneo will be used as the standard.

B. Filter Paper Method

A specified number of weed seeds will be placed on clean moist filter paper in a petri dish and allowed to germinate. Soil that has just been treated with the compound will be added to the petri dish, covering the filter paper and germinating weed seeds. Weed growth in the petri dish will be monitored over a certain time period, such as four days. Three or four replicates will be used and Telone® will be used as the standard. Other experiments using only one type of weed seed and/or other standards can also be performed to determine the herbicidal activity of the pesticides of the present invention to specific types of weeds.

III. Expected Results

It is expected that one or more of the compounds of the present invention will be approximately as effective as Telone® (or other commercial standards) in reducing microbial activity and inhibiting weed seed germination and weed growth.

Conclusion

The above examples demonstrate that the novel biopesticides of the present invention are not only candidates for replacement of currently used biopesticides, but offer a safer, more "environmentally-friendly" and economical alternative as well. As compared with currently available pesticides, the biopesticides of the present invention are equally, or in some cases more effective than the commercial standards.

In the article entitled, "Insect Control Technology," pages 524, 579, Kirk-Othmer Encyclopedia of Chemical Technology, 4th Ed., John Wiley and Sons, Inc., New York, N.Y. (1994), which is hereby incorporated by reference, the toxicity of various standard fumigants against various types of beetles and weevils is compared. A summary of this comparison is shown below in Table 30:

TABLE 32

Comparative Toxicity of Fumigants, $LC_{50}$ for 6 h, mg/L[a]

| Fumigant | Granary weevil, Sito-philus granarius | Drugstore beetle, Stegobium paniceum | Confused flour beetle, Tribolium confusum | Bean, weevil, Acanthoscelides obtectus | Saw-toothed grain weevil, Oryzae philus suri-namensis |
|---|---|---|---|---|---|
| acrylonitrile | 2.0 | 1.7 | 3.0 | 1.1 | 0.8 |
| carbon disulfide | 43.0 | 42.0 | 75.0 | 29.0 | 40.0 |
| chloropicrin | 3.4 | 1.9 | 6.4 | <1.5 | <1.5 |
| ethylene dibromide | 3.0 | 2.8 | 3.4 | 10.2 | 0.9 |
| ethylene dichloride | 127.0 | 77.0 | 53.0 | 49.0 | 39.0 |
| ethylene oxide | 13.5 | 9.0 | 27.5 | 10.5 | 4.0 |
| hydrogen cyanide | 4.6 | <0.4 | 0.8 | 0.9 | <0.4 |
| methyl bromide | 4.8 | 4.4 | 9.2 | 4.2 | 4.4 |

Although the biopesticides of the present invention were not tested against these particular types of pests, the biopesticides have been shown to be at least as or more effective than chloropicrin against the adult house fly and lesser grain borer in many of the fumigation assays as noted above. It is reasonable to conclude, therefore, that the various natural and synthetic fumigants of the present invention are at least as or more effective than these other standard fumigants as well in killing other pests, including, but not limited to the granary weevil, drugstore beetle, confused flour beetle, bean weevil, and saw-toothed grain weevil.

Most of the fumigants in Table 32 have been banned or heavily restricted. In the future, natural fumigants (or closely related analogs and derivatives) may be widely used, even if they are less toxic than methyl bromide, chloropicrin or phosphine gas. In those cases where the biopesticides of the present invention may not be as effective as the commercial compounds when used as a fumigant, it is possible these pesticides can be used as contact or topical pesticides by applying the biopesticide directly onto the vertebrate animal such that when the target pest comes in contact with the biopesticide, it is killed or slowed. The biopesticide can alternatively be incorporated into food for the pests as a type of bait or dietary pesticide. Or, the biopesticide can be used or dispersed in water to kill target aquatic pests.

It is further known that structure-activity relationships (SAR's) can be determined with mass synthesis to develop an optimized potent pesticide or biopesticide. SAR refers to determination of the relationships between the structure of a compound and its biological activity. This is accomplished by first determining the most important chemical properties of a series of related compounds. This includes, but is not limited to the lipophilicity, volatility, size, shape, and electronegativity of the compounds. The relationship between the toxicity and one of the above properties is then evaluated.

In the present invention, there has been observed a strong positive correlation between the volatility of a cyanohydrin and its toxicity as a fumigant. The lower molecular weight groups on the cyanohydrin produce analogs or derivatives that are more effective as fumigants. The derivatives that contain a phenyl ring (e.g., cinnamate or fluorobenzoate) or a long carbon chain (e.g., citronellate or decanoate) or analogs that contain a phenyl ring (e.g., mandelonitriles, cinnamyl cyanohydrin) or a carbon chain longer than 10-carbons (e.g. citryl or citronellyl cyanohydrin) are not as effective as dimethyl ketone cyanohydrin and CHP acetate, for example.

It is predicted, on this basis, that cyanohydrins synthesized from fluoroacetone, cyclobutenone, diethyl ketone, propionaldehyde, propenal, methyl ethynyl ketone, and others including, but not limited to analogs of CHP wherein one or more hydrogen atoms on CHP are removed or replaced with other groups such as a halogen, carboxy or carbonyl group, will be highly effective and very potent pesticides, particularly as fumigants, against pests, including insects, nematodes, plants, bacteria and fungi. It may be that these biopesticides can also be used to control diseases, including, but not limited to, the diseases controlled by methyl bromide and other well-known pesticides.

Biopesticides have the further advantage of fast-track Federal registration, with considerable lower cost and time commitment as compared with synthetic pesticides. Further, some of the biopesticides, such as certain CHP-derivatives, (e.g., CHP acetate and CHP pivalate) offer a potentially longer shelf-life than conventional biopesticides because of their structure. Specifically, the ester is less reactive than the cyanohydrin, but the ester will be hydrolyzed in the insect or nematode, thereby releasing the toxophore, CHP.

The biopesticides of the present invention are less toxic to humans and vertebrate animals than traditional pesticides such as organochlorines or organophosphorus compounds, or the traditional fumigants such as methyl bromide, dibromochloropropane or dichlorvos. Specifically, the biopesticides of the present invention are all rapidly biodegradable, quickly excreted by vertebrates, and pose virtually no residual threat in soil or water.

Although the present invention has been described in considerable detail with reference to certain preferred versions thereof, other versions are possible. For example, although some of the analogs were not volatile enough to be effective fumigants, other routes of exposure are still possible including contact toxicity, dietary toxicity, and toxicity through contact with treated water. Further, although not all CHP-derivatives and analogs or monoterpenoid/cyanohydrin hybrids were tested, it is likely that many of these other compounds will also possess high efficacy against pests, including plants, animals, bacteria, fungus, and so forth, as defined herein, and perhaps even disease.

Therefore, the spirit and scope of the appended claims should not be limited to the description of the preferred embodiments contained herein.

What is claimed:

1. A method for suppressing target pests comprising exposing the pests to an effective biopesticidal amount of a composition, the composition comprising a carrier and purified (S)-1-cyano-2-hydroxy-3-butene (CHB), wherein the purified (S)-l-cyano-2-hydroxy-3-butene is a breakdown product of epi-progoitrin, the epi-progoitrin isolated from a crambe plant or mustard plant, further wherein the target pests are plants, bacteria, fungi or root knot nematodes.

2. The method as recited in claim 1 wherein the target pests are weed seeds or weeds.

3. The method as recited in claim 1 wherein the fungi, are selected from the group consisting of true fungi, molds, rusts, mildews, smuts and mushrooms.

4. The method as recited in claim 1 wherein the target pests are the eggs or larvae of the root-knot nematodes.

5. The method as recited as recited in claim 1 wherein the bacteria are selected from the group consisting of Agrobacterium, Corynebacterium, Erwinia, Pseudomonas, Xanthomonas, Rizobium and Streptomyces.

6. The method as recited in claim 1 wherein the target pests are exposed to the biopesticide by fumigation or contact.

7. The method as recited in claim 1 wherein the target pests are exposed to the biopesticide by dietary or aquatic means.

8. The method as recited in claim 1 wherein the target pests are exposed to the biopesticide by fumigation or contact.

9. The method as recited in claim 1 wherein the target pests are exposed to the biopesticide by dietary or aquatic means.

10. A method for suppressing target pests comprising exposing the pests to an effective biopesticidal amount of a composition, the composition comprising a carrier and a closely-related analog of purified 1-cyano-2-hydroxy-3-butene (CHB) wherein the target pests are plants, bacteria, fungi or root knot nematodes, further wherein the closely-related analog is dimethyl ketone cyanohydrin, methyl ethyl ketone cyanohydrin, 3-cyano-3-hydroxy-1-propene, diethyl ketone, isobutyraldehyde, propionaldehyde, cyclobutanone, fluoroacetone, or di-tert-butyl ketone.

11. The method as recited in claim 10 wherein the target pests are weed seeds or weeds.

12. The method as recited in claim 10 wherein the fungi, are selected from the group consisting of true fungi, molds, rusts, mildews, smuts and mushrooms.

13. The method as recited in claim 10 wherein the target pests are the eggs or larvae of the root-knot nematodes.

14. The method as recited as recited in claim 10 wherein bacteria are selected from the group consisting of Agrobacterium, Corynebacterium, Erwinia, Pseudomonas, Xanthomonas, Rizobium and Streptomyces.

15. The method as recited in claim 10 wherein the target pests are exposed to the biopesticide by fumigation or contact.

16. The method as recited in claim 10 wherein the target pests are exposed to the biopesticide by dietary or aquatic means.

17. The method of claim 10 wherein the dimethyl ketone cyanohydrin can be isolated from flax and the methyl ethyl ketone cyanohydrin can be isolated from flax or cassava.

18. The method of claim 10 wherein a starting material for the closely-related analog is isolated from a plant selected from the group consisting of cramble, rapeseed and mustard.

19. A method for suppressing target pests comprising exposing the pests to an effective biopesticidal amount of a composition, the composition comprising a carrier and a closely-related derivative of 3-cyano-3-hydroxy-1-propene, wherein the closely related derivative of 3-cyano-3-hydroxy-1-propene is a carboxyester or alkyl ether, further wherein the target pests are plants, bacteria, fungi or root knot nematodes.

20. The method as recited in claim 19 wherein the target pests are weed seeds or weeds.

21. The method as recited in claim 19 wherein the fungi, are select from the group consisting of true fungi, molds, rusts, mildews, smuts and mushrooms.

22. The method as recited in claim 19 wherein the target pests are the eggs or larvae of the root-knot nematodes.

23. The method as recited as recited in claim 19 wherein the bacteria are selected from the group consisting of Agrobacterium, Corynebacterium, Erwinia, Pseudomonas, Xanthomonas, Rizobium and Streptomyces.

24. The method of claim 19 wherein a starting material for the closely-related derivative is isolated from a plant selected from the group consisting of crambe, rapeseed and mustard.

* * * * *

UNITED STATES PATENT AND TRADEMARK OFFICE
CERTIFICATE OF CORRECTION

PATENT NO. : 6,545,043 B1
DATED : April 8, 2003
INVENTOR(S) : Gregory L. Tylka et al.

It is certified that error appears in the above-identified patent and that said Letters Patent is hereby corrected as shown below:

<u>Title page, Item [54] and Column 1, Line 2,</u>
Title, insert -- NOVEL -- before "COMPOUNDS".
Item [56], References Cited, OTHER PUBLICATIONS, delete "Wshington" and insert --Washington -- therefor.

<u>Column 4,</u>
Line 41, delete "INVENTION" and insert -- DRAWINGS -- therefor.
Line 50, delete "DRAWINGS" and insert -- INVENTION -- therefor.

<u>Column 7,</u>
Line 66, delete "nitrites" and insert -- nitreles -- therefor.

<u>Column 9,</u>
Line 5, delete "$CH_2=CH-CH_2-C=N$ (AC)" and insert --$CH_2=CH-CH_2-C\equiv N$ (AC) -- therefor.

<u>Column 11,</u>
Line 65, delete "." after "also".

<u>Column 12,</u>
Line 41, delte "In" and insert -- in -- therefor.

<u>Column 13,</u>
Line 27, delete (CMP) and insert -- (CHB) -- therefor.
Line 61, under "TABLE 3", delete "1680-1620" below "2260" and insert -- 1680 –1620-- below "2260-2240" therefor.

<u>Column 16,</u>
Line 51, insert --")"-- after (1991).
Line 54, insert --")"-- after (1991).

<u>Column 17,</u>
Line 51, delete "rootworir" and insert -- rootworm -- therefor.

<u>Column 19,</u>
Line 45, delete 1 2A" and insert --12A-- therefor.

UNITED STATES PATENT AND TRADEMARK OFFICE
CERTIFICATE OF CORRECTION

PATENT NO. : 6,545,043 B1
DATED : April 8, 2003
INVENTOR(S) : Tylka et al.

It is certified that error appears in the above-identified patent and that said Letters Patent is hereby corrected as shown below:

Column 20,
Line 45, delete "NA2SO$_4$" and insert -- NA$_2$SO$_4$ -- therefor.
Line 52, "CyAno" and insert -- Cyano -- therefor.

Column 21,
Line 52, delete "10" after "topical".

Column 22,
Line 40, delete "them" and insert -- then -- therefor.

Column 26,
Line 55, delete "CIP" and insert -- CHP -- therefor.

Column 27,
Line 37, delete "CBP" and insert -- CHP -- therefor.

Column 28,
Line 2, delete "CBP" and insert -- CHP -- therefor.
Line 38, delete "he" and insert -- The -- therefor.
Line 63, delete "compounds" and insert -- compound -- therefor.

Column 29,
Line 66, delete "CHI)" and insert -- CHP -- therefor.
Line 67, delete "chiorpyrifos" and insert -- chlorpyrifos -- therefor.

Column 31,
Line 19, delete "CBp" and insert -- CHP --

Column 32,
Line 19, delete "CHR" and insert -- CHB --

Column 34,
Line 30, delete "oncentrations" and insert -- Concentrations --.

UNITED STATES PATENT AND TRADEMARK OFFICE
CERTIFICATE OF CORRECTION

PATENT NO.    : 6,545,043 B1
DATED         : April 8, 2003
INVENTOR(S)   : Gregory L. Tylka et al.

It is certified that error appears in the above-identified patent and that said Letters Patent is hereby corrected as shown below:

Column 36,
Line 54, insert -- Tables 25 and 26 show the total bacterial count and fungi count, respectively, after two days, with no treatment of the soil (blank control and solvent control) and with treatments using various concentrations of CHP-Acetate. -- below "A. Bacteria and Fungi Study".

Column 37,
Line 61, delete "can" after "also".

Column 38,
Line 16, under "TABLE 30", delete "Telone$^{TM}$" and insert -- Telone$^®$ -- therefor.
Line 30, delete "can" after "also".

Column 39,
Line 35, delete "Teloneo" and insert --Telone$^®$ -- therefor.

Column 40,
Line 2, delete "30" after "Table" and insert --32-- therefor.

Column 41,
Line 61, delete second instance of "as recited" after "method".

Column 42,
Line 27, delete "as recited" after "method".
Line 42, delete "cramble" and insert -- crambe -- therefor.
Line 54, delete "select" and insert -- selected -- therefor.
Line 58, delete second instance of "as recited" after "method".

Signed and Sealed this

Third Day of August, 2004

JON W. DUDAS
*Acting Director of the United States Patent and Trademark Office*